United States Patent [19]
Robinson et al.

[11] Patent Number: 5,961,546
[45] Date of Patent: *Oct. 5, 1999

[54] METHOD AND APPARATUS FOR RECAPTURE OF HOOKED ENDOPROSTHESIS

[75] Inventors: Timothy Robinson, Sandown, N.H.; Michael Weiser, Groton, Mass.

[73] Assignee: C.R. Bard, Inc., Murray Hill, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/839,404

[22] Filed: Apr. 11, 1997

Related U.S. Application Data

[62] Division of application No. 08/803,839, Feb. 24, 1997, which is a continuation of application No. 08/306,874, Sep. 15, 1994, abandoned, which is a continuation-in-part of application No. 08/147,498, Nov. 4, 1993, abandoned, and a continuation-in-part of application No. 08/051,728, Apr. 22, 1993, abandoned.

[51] Int. Cl.⁶ ........................................................ A61F 2/06
[52] U.S. Cl. ................................................................ 623/1
[58] Field of Search .................................. 623/1, 11, 12; 606/194, 195

[56] References Cited

U.S. PATENT DOCUMENTS 4,562,596  1/1986  Kornberg .
4,793,348  12/1988  Palmaz .

(List continued on next page.)

FOREIGN PATENT DOCUMENTS 0466518  1/1992  European Pat. Off. .
0539237  4/1993  European Pat. Off. .
0556850  8/1993  European Pat. Off. .
0579523  1/1994  European Pat. Off. .
0657147  6/1995  European Pat. Off. .
0696447  2/1996  European Pat. Off. .
0701800  3/1996  European Pat. Off. .
511880   8/1991  Japan .
1457921  2/1989  U.S.S.R. .
WO9509586  4/1995  WIPO .
WO9624308  8/1996  WIPO .
WO9717911  5/1997  WIPO .
WO9717912  5/1997  WIPO .
WO9717913  5/1997  WIPO .
WO9726936  7/1997  WIPO .

OTHER PUBLICATIONS

A Self–Expanding Bifurcated Endovascular Graft for Abdominal Aortic Aneurysm Repair, An Initial Study in a Canine Model, J ASAIO. vol. 42, Wilson et al., Sep. 1996, pp. M386–M393.

Infrarenal Aortic Aneurysm Structure: Implications for Transfemoral Repair, J Vasc Surg. vol. 20, issue 1, Chuter et al., Jul. 1994, pp. 44–50.

Transfemoral Insertion of a Bifurcated Endovascular Graft for Aortic Aneurysm Repair: The First 22 Patients, J Cardiovasc Surg. vol. 3, issue 2, Chuter et al., Apr. 1995, pp. 121–128.

Bifurcated Stent–Grafts for Endovascular Repair of Abdominal Aortic Aneurysm, J Surg. Endosc. vol. 8, issue 7, Chuter et al., Jul. 1994, pp. 800–802.

(List continued on next page.)

Primary Examiner—Michael J. Milano
Attorney, Agent, or Firm—Arthur Z. Bookstein

[57] ABSTRACT

An endoprosthesis assembly adapted to be securely positioned within a body lumen is provided with one or more hooks adapted to engage tissue that defines the body lumen. The endoprosthesis includes a resilient self-expanding anchor attached to the tubular graft. The anchor and hooks carried by the anchor are constructed to enable the endoprosthesis to be recaptured in a delivery device to enable repositioning or removal of the endoprosthesis and any time prior to complete deployment of the endoprosthesis in the patient.

14 Claims, 19 Drawing Sheets

U.S. PATENT DOCUMENTS

| | | | |
|---|---|---|---|
| 5,035,706 | 7/1991 | Gianturco | 606/198 |
| 5,059,205 | 10/1991 | El-Nounou et al. . | |
| 5,104,399 | 4/1992 | Lazarus . | |
| 5,219,355 | 6/1993 | Parodi et al. . | |
| 5,242,462 | 9/1993 | El-Nounou et al. . | |
| 5,275,622 | 1/1994 | Lazarus et al. . | |
| 5,282,824 | 2/1994 | Gianturco . | |
| 5,290,305 | 3/1994 | Inoue . | |
| 5,330,500 | 7/1994 | Song | 623/1 |
| 5,354,308 | 10/1994 | Simon et al. . | |
| 5,360,443 | 11/1994 | Barone et al. . | |
| 5,375,612 | 12/1994 | Cottenceau . | |
| 5,383,892 | 1/1995 | Cardon et al. . | |
| 5,387,235 | 2/1995 | Chuter . | |
| 5,449,373 | 9/1995 | Pinchasik | 623/1 |
| 5,456,713 | 10/1995 | Chuter . | |
| 5,489,295 | 2/1996 | Piplani et al. . | |
| 5,562,726 | 10/1996 | Chuter . | |
| 5,591,195 | 1/1997 | Taheri | 623/1 |
| 5,628,788 | 5/1997 | Pinchuk . | |
| 5,639,278 | 6/1997 | Dereume et al. . | |

OTHER PUBLICATIONS

Evolution of Technologies in Endovascular Grafting, J Cardiovasc Surg. vol. 3, issue 2, Green et al., Apr. 1995, pp. 101–107.

Rollins et al., "Self Expanding Metallic Stents: Preliminary Evaluation . . . ", Radiology, Jun. 1987, pp. 739–742.

Mirich et al., "Percutaneously Placed Endovascular Grafts for Aortic Aneurysms . . . ", Radiology, Mar. 1989, pp. 1033–1037.

Lawrence, Jr. et al., "Percutaneous Endovascular Graft: Experimental Evaluation", Radiology, May 1987, pp. 357–360.

Dobben et al., "Prostatic Urethra Dilatation with the Gianturco Self–Expanding Metallic Stent . . . ", AJR, Apr. 1991, pp. 757–761.

Irie et al., "Relocatable Gianturco Expandable Metallic Stents", Radiology, vol. 178, No. 2, pp. 575–578.

Yoshioka et al., Self–Expanding Endovascular Graft: An Experimental Study in dogs, AJR:151, Oct. 1988, pp. 673–676.

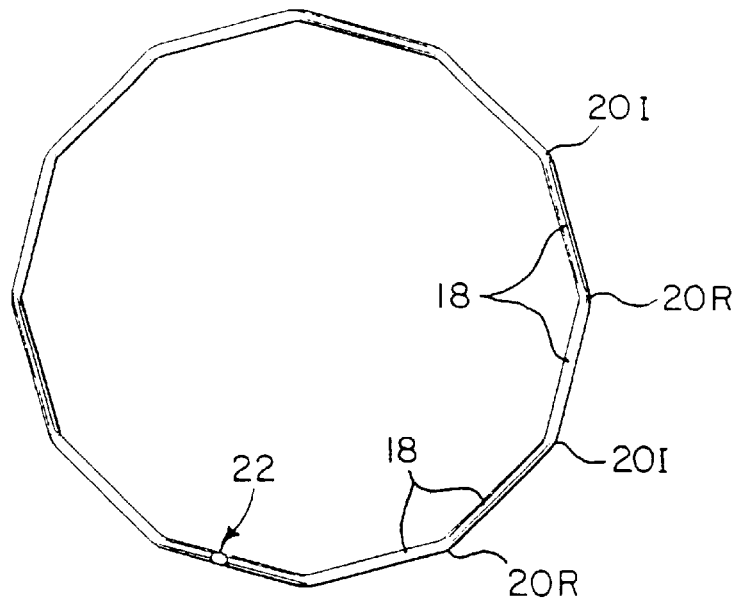
Fig. 4
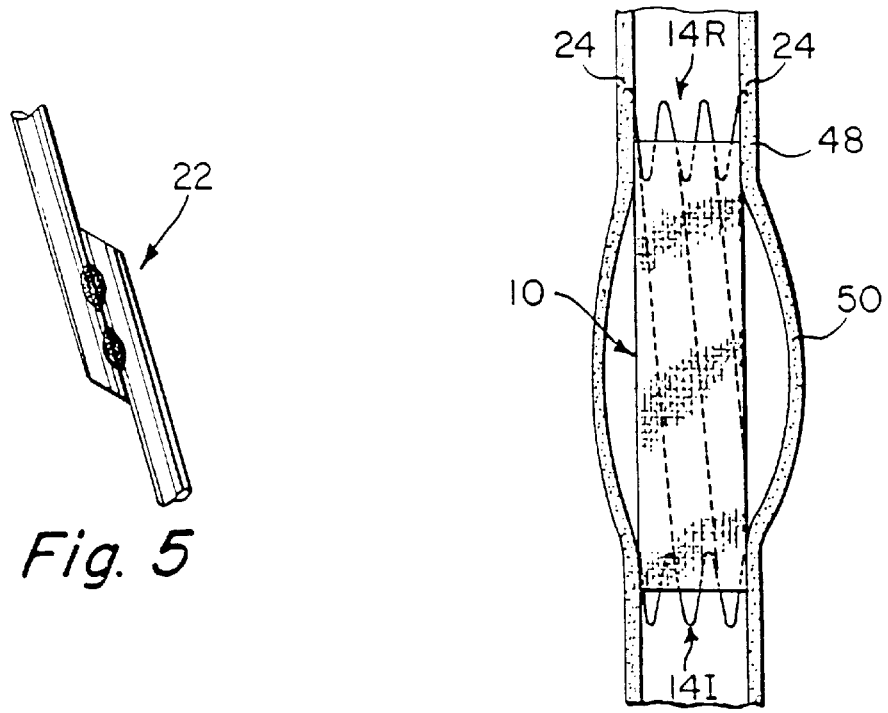
Fig. 5
Fig. 6

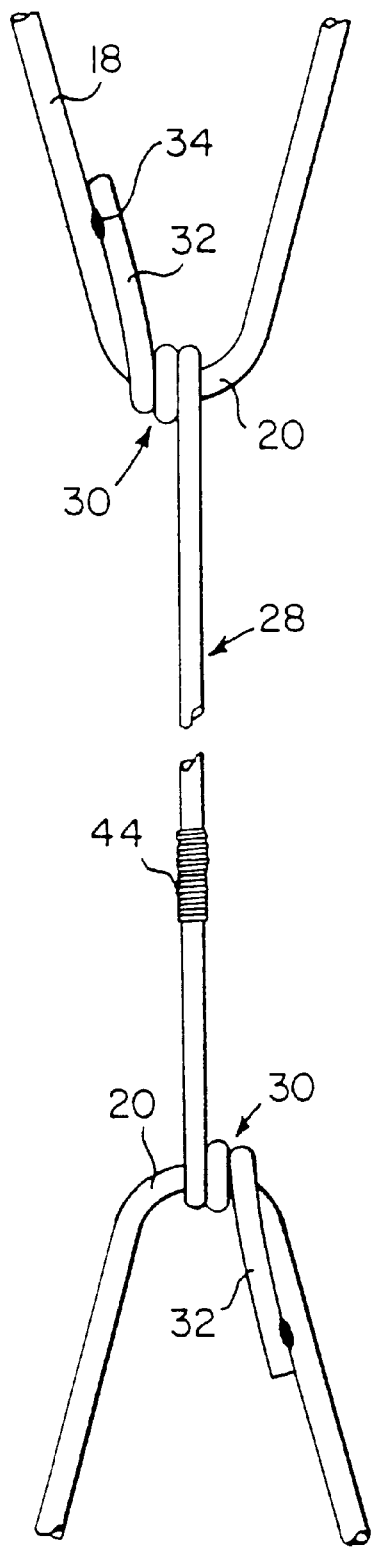
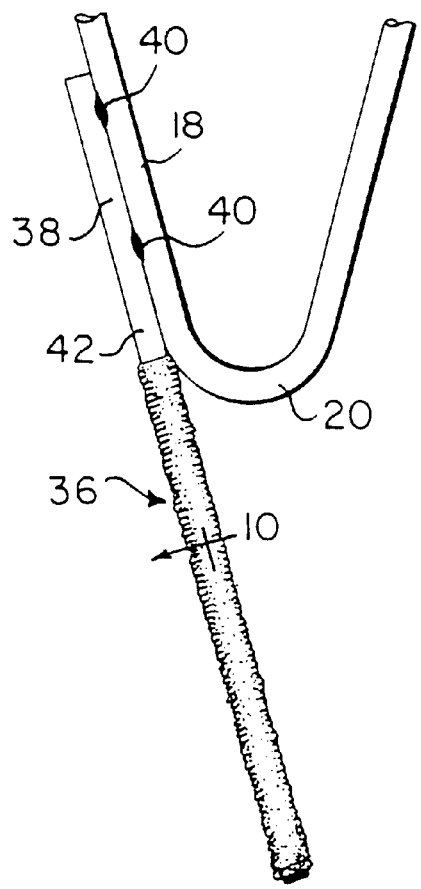
Fig. 9
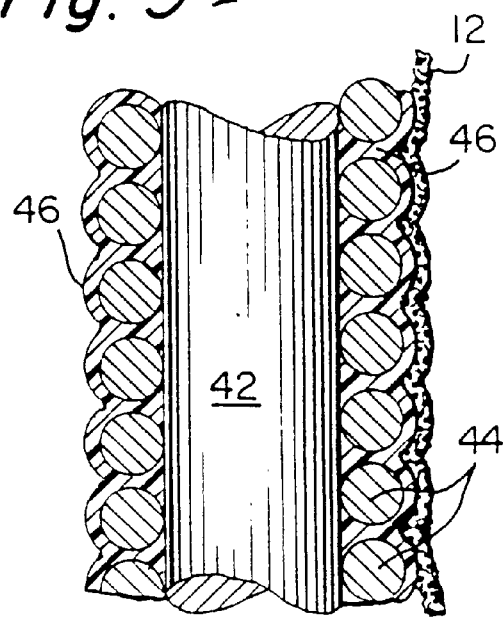
Fig. 10
Fig. 8

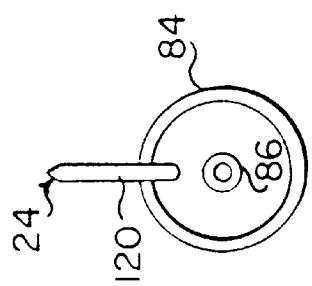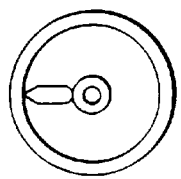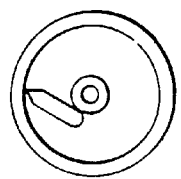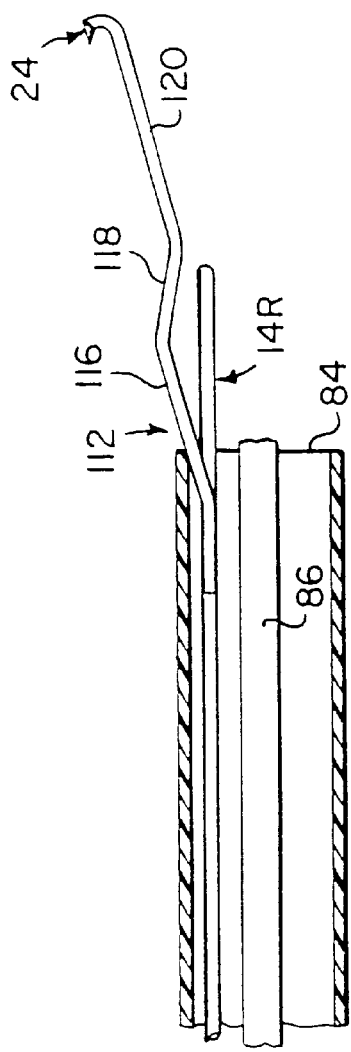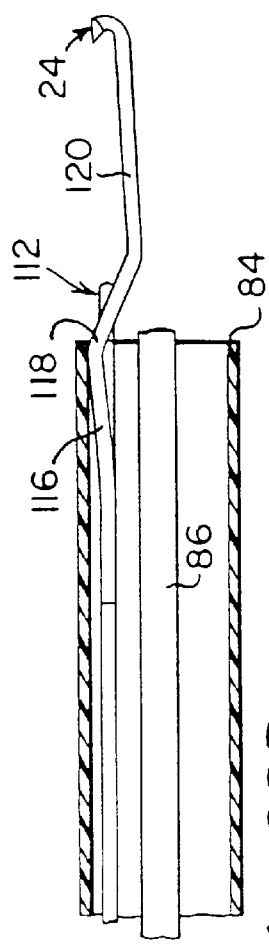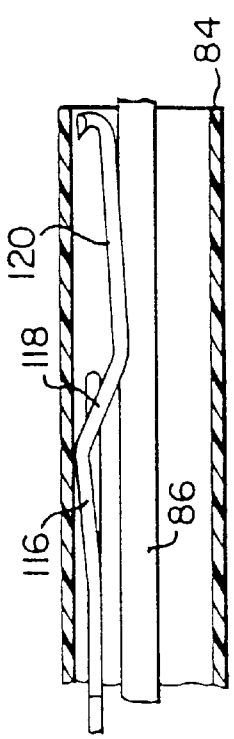

METHOD AND APPARATUS FOR RECAPTURE OF HOOKED ENDOPROSTHESIS

RELATED APPLICATIONS

This is a divisional of application Ser. No. 08/803,839, filed on Feb. 24, 1997, which is a file wrapper continuation of Ser. No. 08/306,874 filed Sep. 15, 1994, now abandoned which is a continuation-in-part of applications Ser. No. 08/147,498, filed Nov, 4, 1993, now abandoned and Ser. No. 08/051,728, filed Apr. 22, 1993, now abandoned.

FIELD OF THE INVENTION

The present invention relates to devices and techniques for placing and securing a tubular endoprosthesis in a predetermined location in a patient's body.

BACKGROUND OF THE INVENTION

It has been long accepted practice to treat a variety of vascular disorders in a surgical procedure that involves placement of a tubular endoprosthesis, such as a graft, in a patient's vascular system. The construction and characteristics of the graft typically will be adapted to optimize its use in the specific surgical environment and condition to be treated and, accordingly, a number of different types of grafts are available. Among the most common types of vascular grafts are those formed from a woven or knitted tubular fabric as well as non-fabric tubes such as expanded polytetrafluoroethylene. Such grafts typically are placed in a patient's vascular system in an extensive surgical procedure. In general, the complexity of the surgical procedure required to place the graft will depend on many factors, including the location and surgical accessibility of the portion of the patient's vasculature where the graft is to be placed.

Not all vascular conditions in which it would be desirable to place a graft can be so treated. Among the particularly troublesome medical conditions in which it is desirable to place a graft is that of an abdominal aortic aneurysm, in which a portion of the patient's aorta, the major artery carrying blood from the heart, has developed a weakened wall such that the weakened portion will tend to expand under the influence of the patient's blood pressure. An aortic aneurysm presents a life threatening risk that the aneurysm may burst causing massive internal bleeding. Treatment of the condition typically has involved deeply invasive abdominal surgery in which the patient's abdominal cavity is opened to reach and expose the aortic aneurysm. While maintaining the patient on an independent life support system, the region of the aneurysm is incised lengthwise to enable insertion of the graft into the aorta to span the weakened region and define a structurally tubular flow path between the remaining healthy portions of the aorta. The graft so positioned then is sutured in place. The graft thus serves as a reinforcing liner for the weakened portion of the aorta. Such surgical procedures have been characterized by a relatively high mortality and morbidity rate. Typically, patients suffering from the condition are elderly and are less able to survive the rigors of major abdominal surgery. Additionally, there is a substantial degree of risk when the abdominal cavity is opened because the confining pressure of other abdominal organs on the aorta is released. In some cases, the abdominal wall in the region of the aneurysm is so weak that upon release of the confining pressure, the aneurysm bursts with resulting immediate massive hemorrhaging.

The difficulties and risks associated with the placement of a graft to reinforce an abdominal aortic aneurysm may be reduced significantly by using an endoprosthesis that can be inserted into the patient's blood vessel percutaneously and without requiring extensive surgery. Such devices, and delivery systems for their percutaneous placement are disclosed in the above-identified U.S. patent applications. Those devices include an endoprosthesis having an elongate flexible tubular graft attached to one or more anchors that support the flexible graft and serve to retain the graft in the deployed location in the blood vessel with reduced risk of the graft migrating from its deployed position. The anchor(s) is radially contractible and expandable between a reduced diameter, low profile configuration in which it can be inserted percutaneously into the patient's blood vessel and an expanded configuration in which the anchor(s) is deployed in the blood vessel and engages the inner luminal surface of the blood vessel sufficiently and in a manner to reduce the risk of the graft assembly migrating from its deployed location. In order to further reduce the risk of migration, the device may be provided with one or more hooks that can engage the wall of the blood vessel when the anchor is expanded. Although the use of such hooks is considered to be highly desirable, they may present some difficulty when the device is contracted to a deliverable configuration. The hooks which should extend radially outwardly, may become caught on a portion of the delivery device or may become caught with each other as the device is radially contracted. That may present difficulty when the device is deployed in the patient's blood vessel. Should any of the hooks become caught, that may impair the ability of the device to be properly expanded and may interfere with the ability of the device to be positioned initially or repositioned by the delivery device.

As described in the above-identified pending patent applications, the delivery system includes an elongate, flexible catheter-like device having a tubular sheath at its distal end (the end inserted into the patient). When the endoprosthesis is contracted radially, it can be contained within the sheath of the delivery device. The delivery device then is inserted into the patient either percutaneously or by surgical access and is navigated to the intended placement site. The endoprosthesis then can be ejected from the sheath and can expand to its deployed configuration. As described in further detail in pending application Ser. No. 08/147,498, the device may be only partially ejected from the delivery sheath to permit the physician to verify that the endoprosthesis is in its intended position. If so, the endoprosthesis can be fully released. If not, the endoprosthesis can be withdrawn into the sheath, the sheath can be repositioned, and the endoprosthesis can be again released at the intended location or totally removed from the patient.

It would be desirable, therefore, to provide an endoprosthesis and delivery system therefor that provides the advantages of using hooks to securely engage the blood vessel wall but in which the hooks can be easily disengaged from and reengaged with the blood vessel wall and with reduced risk of the hooks becoming entangled themselves or with other portions of the device and without hindering the deployment and repositioning of the endoprosthesis. It is among the general objects of the invention to provide such a devices and technique for their use.

SUMMARY OF THE INVENTION

The endoprosthesis of the present invention includes an elongate flexible tubular graft and an anchor assembly that includes one or more radially expandable anchors attached to the graft to support the graft as well as to anchor the graft in its intended position in the body lumen. The graft may be formed from materials embodying graft structures conventionally used as artificial vascular grafts. The anchor assembly may be formed from resilient wire arranged to define a generally tubular configuration. The anchor assembly is resilient and can be compressed to a low profile (small diameter) from which it can expand resiliently to an enlarged diameter. The anchor assembly may include one or more anchors formed from a single continuous wire bent in a zigzag configuration to define an alternating series of elongate wire segments connected by bends. The anchor assembly is attached to the graft so that an end of the assembly protrudes axially beyond the ends of the graft to enable the protruding ends of the anchor to engage the wall of the body lumen when the device is deployed in the patient. The anchor assembly may take the form of a single anchor in which its elongate wire segments are longer than the length of the graft so that the ends of the single anchor can protrude from the ends of the graft or may comprise two shorter anchors attached to the respective ends of the graft. When two anchors are employed, they preferably are connected by elongate wire struts that extend along the length of the graft.

In accordance with the present invention, the endoprosthesis is provided with one or more sharp hooks adapted to protrude radially outwardly and configured so that when the device is deployed, the hooks will engage the luminal wall of the body lumen. Such engagement enhances the security of the attachment of the anchor in the body lumen and improves the resistance of the anchor to migration once the endoprosthesis is properly placed. The hooks preferably are formed on the end of short segments of wire that are secured to the anchor. In the preferred embodiment, the hooks extend a short distance beyond the bends of the anchor.

The graft assembly can be delivered with a catheter-like delivery device that includes a tubular outer sheath and an inner positioning member that extends through the sheath. The distal end of the sheath may be formed to define a tubular pod. The endoprosthesis is compacted to its low profile configuration and is loaded into the open distal end of the pod. The delivery device may be inserted into the patient's body lumen, such as a blood vessel, and then is advanced through the patient's vascular system to the intended deployment site. The positioning member has a lumen adapted to receive a guidewire. When the delivery system and graft assembly have been advanced to the intended site of deployment, the positioning member is held stationary while the sheath is withdrawn. As the sheath is withdrawn to progressively expose the anchor, the anchor expands resiliently. The hooks similarly expand radially outwardly toward and into engagement with the wall of the body lumen. With the implant partially deployed, radiopague contrast liquid may be injected through the lumen in the sheath to determine the position of the implant and to determine if the anchor is properly and firmly engaged with the vessel wall.

Among the important aspects of the invention is the arrangement by which the hooks are attached to the anchor. In one aspect of the invention, it is important that the hooks have a wide range of radial movement between the intended expanded, deployed configuration of the device, in which the hooks must protrude radially outwardly of the remaining portions of the anchor and the contracted low profile configuration of the device in which the hooks necessarily are brought together in order that they, together with the other parts of the endoprosthesis, can be withdrawn into the sheath to permit intraluminal delivery. In accordance with one aspect of the invention, the hooks are arranged so that when the device is contracted to its low profile configuration, the hooks will be disposed radially inwardly of the luminal diameter of the pod and, preferably, radially inwardly of the anchor. Moreover, the hooks are attached to and supported relative to the anchor to assure that the hooks will not become caught on the pod as they are withdrawn into the pod and further, to avoid the hooks becoming entangled with each other. In another aspect of the invention, the distal end of the pod may be configured to mate with the hooks so that the hooks, although not drawn into the pod, are engaged with the sheath in a manner that protects the sharp ends of the hook and precludes them from exposure in a manner that could cause injury or difficulty in the placement, repositioning or removal of the endoprosthesis.

In a significant aspect of the invention, the hooks are constructed and attached to the anchors in a manner that enables them to be retracted into the delivery sheath, even after the device has been partially deployed with the hooks in engagement with the tissue of the body lumen.

In several embodiments of the invention, the hooks are attached to or formed on the ends of hook supports that are configured and attached to the anchors in a manner that provides a camming effect between the hook supports and the delivery device. The camming arrangement is such that as the hook supports are drawn into the pod, they will engage the pod in a camming action that draws the hooks radially inwardly of the lumen of the pod. In one specific embodiment, camming elements carried by and extend transversely of the hook support are arranged to chordally engage the inner surface of the pod thereby to draw the hook support and the hook radially inwardly. In this embodiment the transversely extending camming elements may be defined by an S-shaped segment formed within the hook support. In another embodiment, the hook support is bent along its length to define an in-line camming surface that progressively engages the end of the pod as the device is drawn into the pod. In still another embodiment of the invention, the hook support is pivotally attached to the anchor in a manner that enables the associated hook to pivot between a radially outwardly projecting configuration in which the hook can engage the tissue of the body lumen and a retracted configuration in which the hook can be drawn into the pod. A spring is arranged to bias the pivotable element toward the radially outwardly extending configuration.

In another embodiment of the invention, the rim at the distal end of the pod is configured with an annular flange shaped to engage the hooks so that the hooks can rest on the flange in a manner such that the sharp tips of the hooks, although visible, are protected. In this embodiment, the hooks do not retract into the pod. In a further modification of this embodiment, the pod itself may be retractable within a larger diameter sheath at the distal end of the delivery device. In this modification, the sharp tips are engaged on the annular flange of the inner pod and the inner pod together with the sharp tips are retracted into the outer sheath.

It is among the general objects of the invention to provide an improved system and technique for more securely anchoring and positioning an endoprosthesis within a body lumen.

Another object of the invention is to provide a non-migrating vascular endoprosthesis having hooks engageable with the wall of a body lumen yet in which the hooks can be disengaged to enable the endoprosthesis to be repositioned or removed.

A further object of the invention is to provide an endoprosthesis having radially projectable hooks for engagement with a body lumen and a delivery device for the endoprosthesis in which the hooks can be withdrawn to a configuration where the sharp points of the hooks are not exposed to body tissue.

Another object of the invention is to provide a device of the type described in which the hooks of the endoprosthesis can be withdrawn into the delivery device.

A further object of the invention is to provide an improved technique and apparatus for endovascularly treating a vascular aneurysm, including an aortic aneurysm.

Another object of the invention is to provide an endoprosthesis of the type described and a delivery system therefor that enables percutaneous delivery and deployment of the endoprosthesis.

Another object of the invention is to provide an improved catheter-like device insertable into the human body having a high degree of flexibility.

DESCRIPTION OF THE DRAWINGS

The foregoing and other objects and advantages of the invention will be appreciated more fully from the following further description thereof, with reference to the accompanying drawings wherein:

FIG. 4 is an illustration of the anchor as seen along its longitudinal axis;

FIG. 5 is an illustration of the juncture of the ends of the wire that forms the anchor;

FIG. 6 is a diagrammatic illustration of an embodiment of the invention deployed in a blood vessel across an aneurysm;

FIG. 8 is an enlarged illustration of the manner in which the ends of a strut may be connected to the bends of spaced anchors;

FIG. 9 is an enlarged illustration of the connection between the struts illustrated in FIG. 7 and an associated portion of its anchor;

FIG. 10 is an enlarged sectional illustration of a portion of a strut as seen along the line 10—10 of FIG. 9 and further illustrating the manner in which the strut may be attached to the graft;

FIGS. 28A–28C illustrate the embodiment of FIGS. 25–27 in various stages of retraction;

FIGS. 29A–29C illustrate end views of FIGS. 28A–28C, respectively;

DETAILED DESCRIPTION OF THE INVENTION

Figure 1:
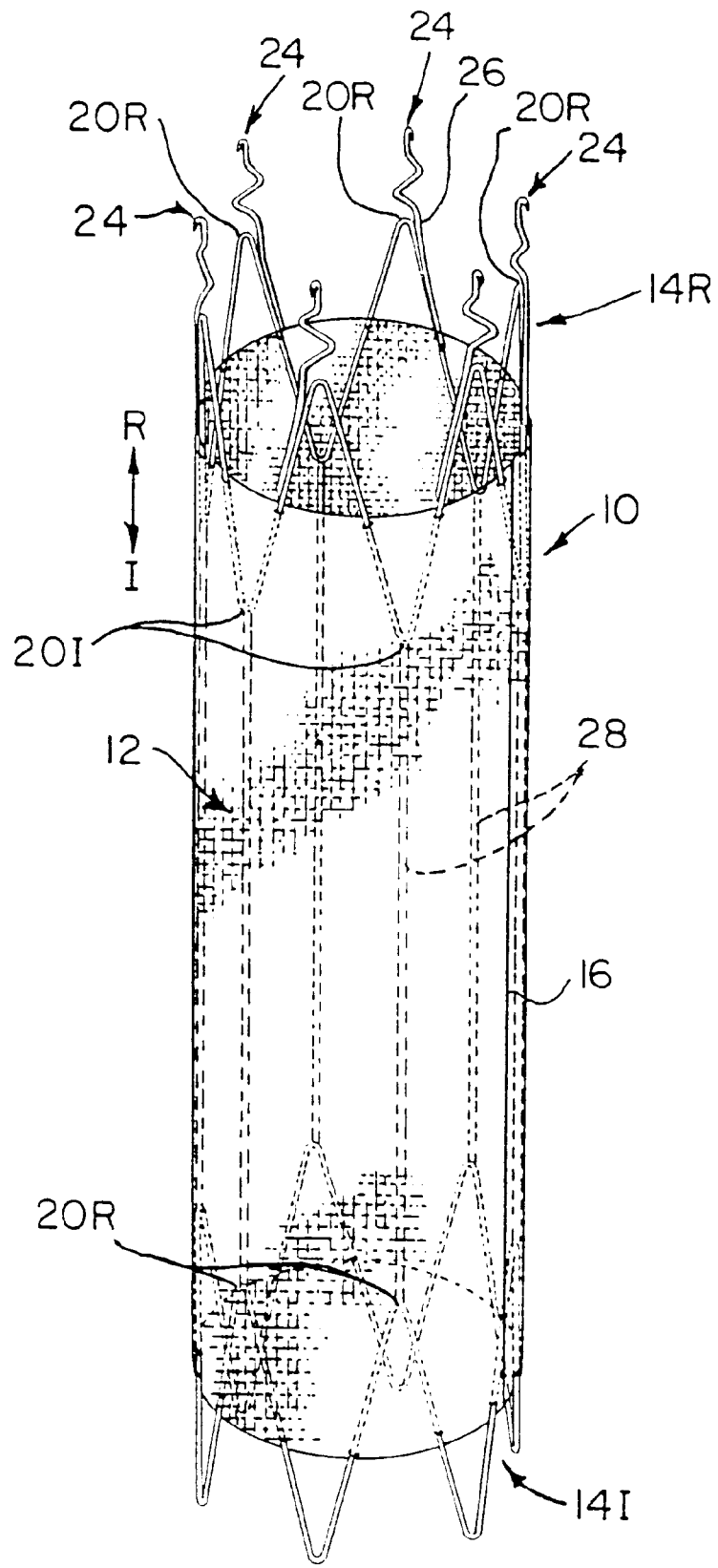
FIG. 1 is an illustration of one embodiment of an endoprosthesis in accordance with the invention.

FIG. 1 illustrates one embodiment of an implantable endoprosthesis assembly indicated generally at 10, adapted for use in the present invention. The endoprosthesis is intended to be placed within a patient's blood vessel, the invention being described, for example, in connection with the treatment of an abdominal aortic aneurysm. For convenience in description, the terms "proximal" and "distal" will refer to directions that are toward the physician or the patient, respectively. Thus, the leading end of the prosthesis that is first inserted into the patient is considered as "distal" while the trailing end, disposed more toward the physician, will be referred to as "proximal". In the context of an abdominal aortic aneurysm, "distal" alternately may be referred to as being in a "renal" direction while "proximal" may be referred to as being in an "iliac" direction.

The assembly 10 includes a synthetic vascular graft 12 and an anchor assembly attached to the graft. The anchor assembly may include a pair of anchors, indicted generally at 14R and 14I in FIG. 1 attached to the ends of the graft. In alternate arrangements, the anchor assembly may include a single elongate anchor element as illustrated and disclosed in U.S. application Ser. No. 08/147,498, the disclosure of which is incorporated by reference herein, in its entirety.

The graft 12 is tubular and may be formed from materials and in any of a variety of constructions known in the art. For example, the graft may be formed from expanded polytetrafluoroethylene with a porosity and internodal distance similar to grafts presently commercially available. Alternately, the graft may be formed from a fabric material, either woven or knitted, or in other configurations known in the art. The graft can be provided with one or more radiopaque stripes 16 to facilitate fluoroscopic or X-ray observation of the graft. The stripes may be formed in the graft by any conventional means as will be appreciated by those skilled in the art.

The anchor assembly is secured to the graft 12 and serves to support and retain the graft in position in the blood vessel. The anchor assembly may be positioned either on the interior or the exterior of the graft.

Figure 2:
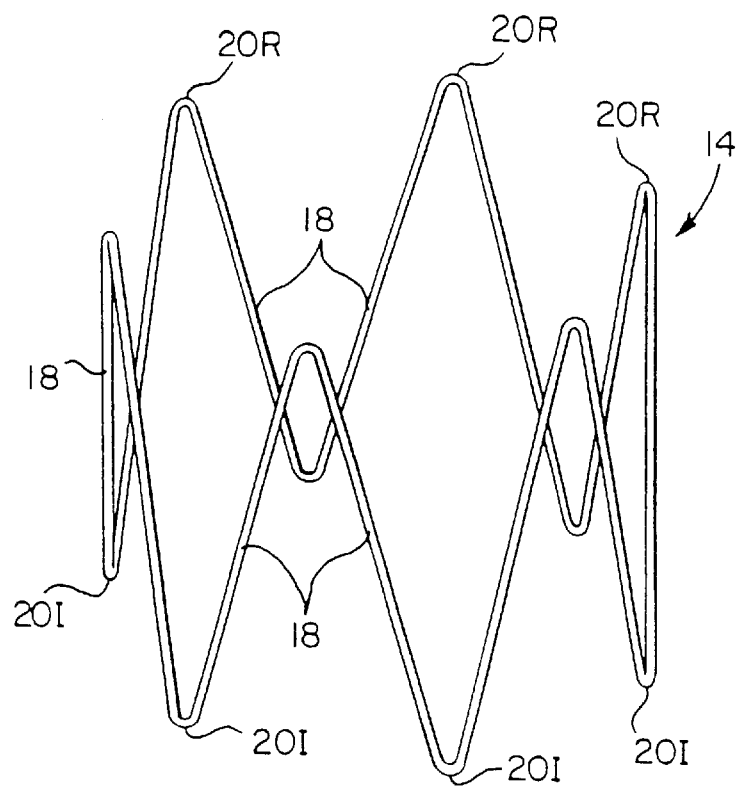
FIG. 2 is an isometric illustration of an anchor that forms a component of the endoprosthesis.
Figure 3:
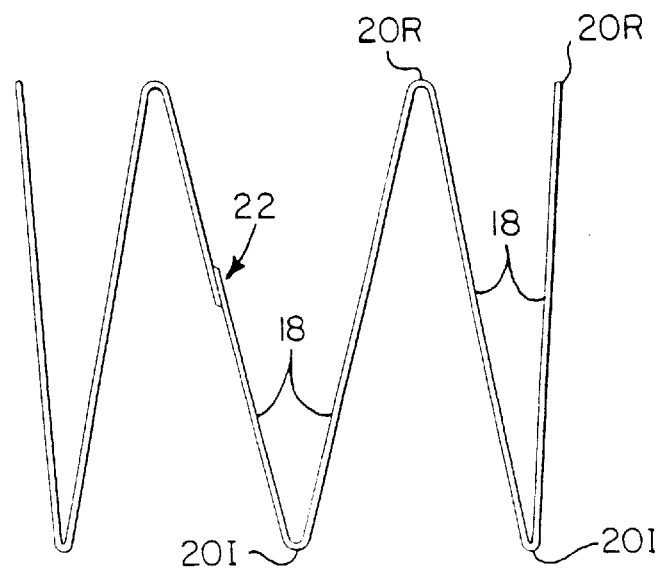
FIG. 3 is a side elevation of one-half of the anchor.

FIG. 2 illustrates a preferred embodiment of the basic structure of the anchor 14. The anchor 14 can be made from a single continuous length of metal wire. The wire preferably may be an alloy of nickel, cobalt, chromium, and molybdenum and may be alloyed in proportions of 35%, 35%, 20% and 10%, respectively. Such wire is commercially available under the designation MP35N. The alloy has high corrosion resistance, is non-magnetic and has a strength comparable to stainless steel. The wire which may be 0.014" diameter is formed to define a zigzag pattern arranged as series of wire segments 18 connected by alternating iliac and renal bends 20I, 20R. The anchor is formed by bending a wire in zigzag configuration then attaching the ends of the wire to each other, as by welding, to form a three dimensional, generally tubular configuration (FIGS. 2–4). FIG. 5 illustrates, in enlarged detail, the juncture 22 of the ends of the zigzag wire. The ends of wire may overlap over a distance of about two millimeters where they are welded. The juncture 22 preferably is formed so that it will be disposed generally intermediate the ends of the wire segment 18 that they define (FIG. 3). For example, for an anchor 14 about twenty-five millimeters long, the juncture 22 may be formed about 12.5 millimeters from one of the ends of the anchor. In an illustrative example, an anchor 14 may have a diameter of the order of thirty-five millimeters, be about twenty-five millimeters long and have twelve wire segments 18 disposed at an angle to each other of about 30°. It should be understood, however, that the dimensions and number of wire segments of the anchor may be varied depending on the size of lumen into which the endoprosthesis is to be placed and the specific condition to be treated. The diameter of the anchor should not be less than the lumen into which it is to be deployed, in order that the anchor may expand the graft fully into engagement with the body lumen. Preferably, the expanded diameter of the anchor may be slightly greater than that of the body lumen. For example, for a body lumen having an effective diameter of the order of 12 to 24 millimeters (as may be encountered in the abdominal aorta), an endoprosthesis having an effective expanded diameter of 14 to 26 millimeters may be desirable. Additionally, it should be noted that it may be desirable to construct the anchor so that it is expandable over a range of diameters so that a single anchor size can be used with a wide range of graft diameters.

The anchor 14 is resilient and can be compressed to a low profile, small diameter configuration suited for percutaneous or surgically assisted (cut-down) delivery into a patient's vascular system. As described in further detail below and in co-pending application Ser. Nos. 08/147,498 and 08/051,728, the endoprosthesis assembly is contained in a slender delivery catheter and is contained in the catheter in a radially contracted low profile configuration in which the anchors are radially compressed to a small effective diameter together with the graft 12. When the assembly 10 is advanced to the site where it is to be implanted, it is released from the delivery device and, as it is released, the anchors expand under the influence of their own resilience to a larger diameter and into engagement with the inner surface of the blood vessel. The anchors press radially outwardly against the inner luminal surface of the blood vessel and serve to retain the endoprosthesis assembly 10 in place.

The security of the engagement between the endoprosthesis and the blood vessel wall may be enhanced by providing at least one, and preferably a plurality, of hooks suggested at 24, on at least one of the anchors, preferably the upstream (distal) anchor 14R. As illustrated in further detail in FIGS. 11, 12 and 25–27, the hooks are formed on the distal ends of hook supports 26. The hook supports preferably are formed from the same material as the main wire of the anchor 14. They are secured along the anchor segments 18, such that the hooks 24 are disposed beyond the renal bends 20R. The hook segments 26 are welded to the anchor segments 18 preferably at two junctions as described in detail in the above-mentioned patent applications. The hooks 24 preferably are sharp and extend radially outward so that they can dig into the vessel wall to prevent migration after the device is implanted. It should be understood that although FIG. 1 illustrates a hook associated with each renal bend 20R, fewer hooks may be adequate.

In the preferred embodiment, the endoprosthesis assembly 10 includes a pair of expandable anchors, including the distal anchor 14R and the proximal anchor 14I. The distal and proximal anchors preferably are joined by longitudinally extending struts 28 that are connected to the two anchors and extend longitudinally of the endoprosthesis 10. In the embodiment as shown in FIG. 1, the struts 28 are attached at their distal ends to the proximal bends 20I of the anchor 14R and at their proximal ends to the distal bends 20R of the proximal anchor 14I. The ends of the struts 28 may be attached to the bends of the anchors 14 by welding or other suitable means. FIG. 8 illustrates one method of strut attachment in this embodiment in which the ends of the strut 28 are wrapped, in coil fashion, about the anchor bends to which they are attached, as indicated at 30. The wire from which the strut is formed defines, at each end, a tail segment 32 that extends partly along the anchor segment 18 adjacent the anchor bend and is attached, as by a weld 34, to that segment 18. The struts may be arranged so that some or all of the struts are disposed either inside or outside of the graft 12, the illustrative embodiments illustrating arrangements in which the struts are disposed completely within the graft.

When disposed outside of the graft, appropriate apertures may be formed in the graft to permit the wires to pass through the graft material.

Figure 7:
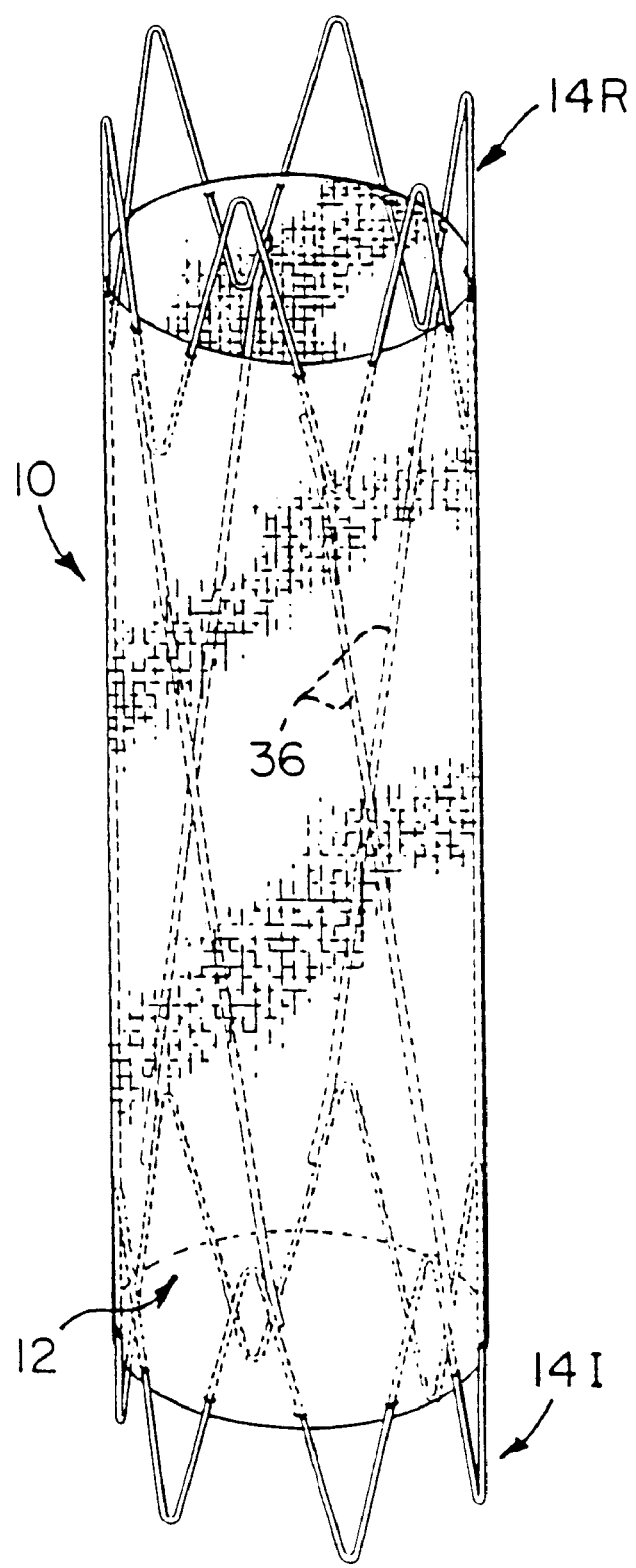
FIG. 7 is an illustration of another embodiment of the endoprosthesis with the hooks not shown for clarity.

FIG. 7 illustrates a preferred embodiment for the arrangement of longitudinal struts in which the struts 36 extend skewed to the longitudinal axis of the endoprosthesis 10. As illustrated in further detail in FIG. 9, in this embodiment, the ends 38 of each strut 36 extend along side and are attached, as by welds 40 to a portion of a wire segment 18 adjacent a bend 20 on the anchor 14. In contrast to the embodiment shown in FIG. 8 in which the ends of the strut 28 are connected to longitudinally aligned anchor bends 20 in the skewed strut arrangement, the ends of a strut are attached to circumferentially displaced portions of segments of the proximal and distal anchors. With this arrangement, the attachment of the struts 36 is simplified, requiring only that the ends of the strut 36 be oriented in skew fashion so that they can be attached to the generally skewed wire segments 18 of the anchors.

FIGS. 9 and 10 also show further details as to the preferred construction for the struts. The struts 28, 36 preferably include an inner core wire 42 surrounded by a helical coil 44 wrapped tightly about the core wire 42. The coil is wrapped in a thin tube of thermoplastic polymeric material. The polymeric layer may comprise polypropylene, applied as a tube about the coil 44 and then heated sufficiently to enable the polypropylene to begin to melt and flow into close intimacy with the turns of the coil 44 that may be applied, for example, in the form of tubing. The polymeric covering 46 may be formed from the same or a different polymeric material from which the graft 12 is formed. The struts may be attached firmly to the graft by heat bonding the polymeric covering directly to the graft material 12, as suggested in FIG. 10. With this arrangement, the struts may be attached securely along their full length to the graft 12 to provide full support for the graft. The same construction may be used in the embodiment illustrated in FIGS. 1 and 8. The core wire 42 and wire from which the helical coil 44 is formed preferably are formed from MP35N alloy and have diameters smaller than 0.012 inches. The two wire construction provides enhanced rigidity after the device is assembled while at the same time allowing the anchor to collapse to a small profile. A strut so constructed is considered to have sufficient radiopacity to permit adequate X-ray or fluoroscopic visualization of the struts when implanted in the abdominal aorta.

In accordance with the invention hooks are provided on the distal end of the endoprosthesis so that the device can more securely engage the vessel into which it is placed to further reduce the risk that the endoprosthesis 10 may migrate from its placement site. When the device is deployed, the hooks are arranged so that they project radially outwardly beyond the outer portions of the endoprosthesis 10 to assure that the hooks will engage securely the tissue of the body lumen. FIG. 6 illustrates diagrammatically, the placement of an endoprosthesis 10 in a portion of a blood vessel such as an aorta 48 having an aneurysm 50. The endoprosthesis 10 has radially expandable anchors 14R, 14I at its respective ends. The upstream end of the device at distal anchor 14R includes radially extending hooks 24 illustrated as being embedded in the wall of the aorta.

In the preferred embodiment of the invention the endoprosthesis is selected so that when fully expanded, it will match or be slightly larger in diameter than the lumen of the vessel into which it is to be implanted. It is intended that when the implant is deployed and expanded, the ends of the graft will lie as close to the surface of the lumen of the blood vessel as possible in order to enhance tissue ingrowth into the graft wall and provide a smooth transition in the surface that defines the flow area from the healthy portion of the blood vessel into the graft. To that end, the anchor should be selected with respect to the grafts so that the relaxed freely expanded anchor will define a diameter greater than the fully expanded diameter of the graft. That assures that when the device is deployed, the anchor will open the end of the graft fully.

An important aspect of the invention relates to the arrangement by which the endoprosthesis 10, including its anchors 14 can be contracted to a low profile configuration in which the endoprosthesis 10 is insertable into and carried by a slender tubular delivery device but without the hooks 24 becoming entangled with each other or otherwise interfering with the ability of the device to be radially contracted or expanded. A significant aspect of the invention relates to the ability of the device to dispose the hooks 24 radially outwardly of at least the end of the endoprosthesis with which the hooks are disposed when the device is deployed yet to draw the hooks radially inwardly of the other portions of the endoprosthesis when the device is contracted. Such ability enables the position of the device to be adjusted within the blood vessel before the device is fully deployed and released from the delivery device. FIGS. 1, 7, 11 and 12 illustrate, in increasingly detail, one embodiment of the arrangement by which the hooks may be disposed between their deployed and contracted configurations. In this embodiment, the hook support 26 is provided with transversely extending elements that may be considered as extending generally tangentially of the endoprosthesis 10 and generally perpendicular to the radially outward direction in which the hook 24 extends. As will be described in further detail below, when the endoprosthesis 10 is drawn into the tubular delivery device, the transverse extensions will engage the tubular delivery device in a manner that draws the hooks 24 radially inwardly to a position within and spaced from the inner circumference of the receptive lumen of the delivery device.

Figures 11, 12:
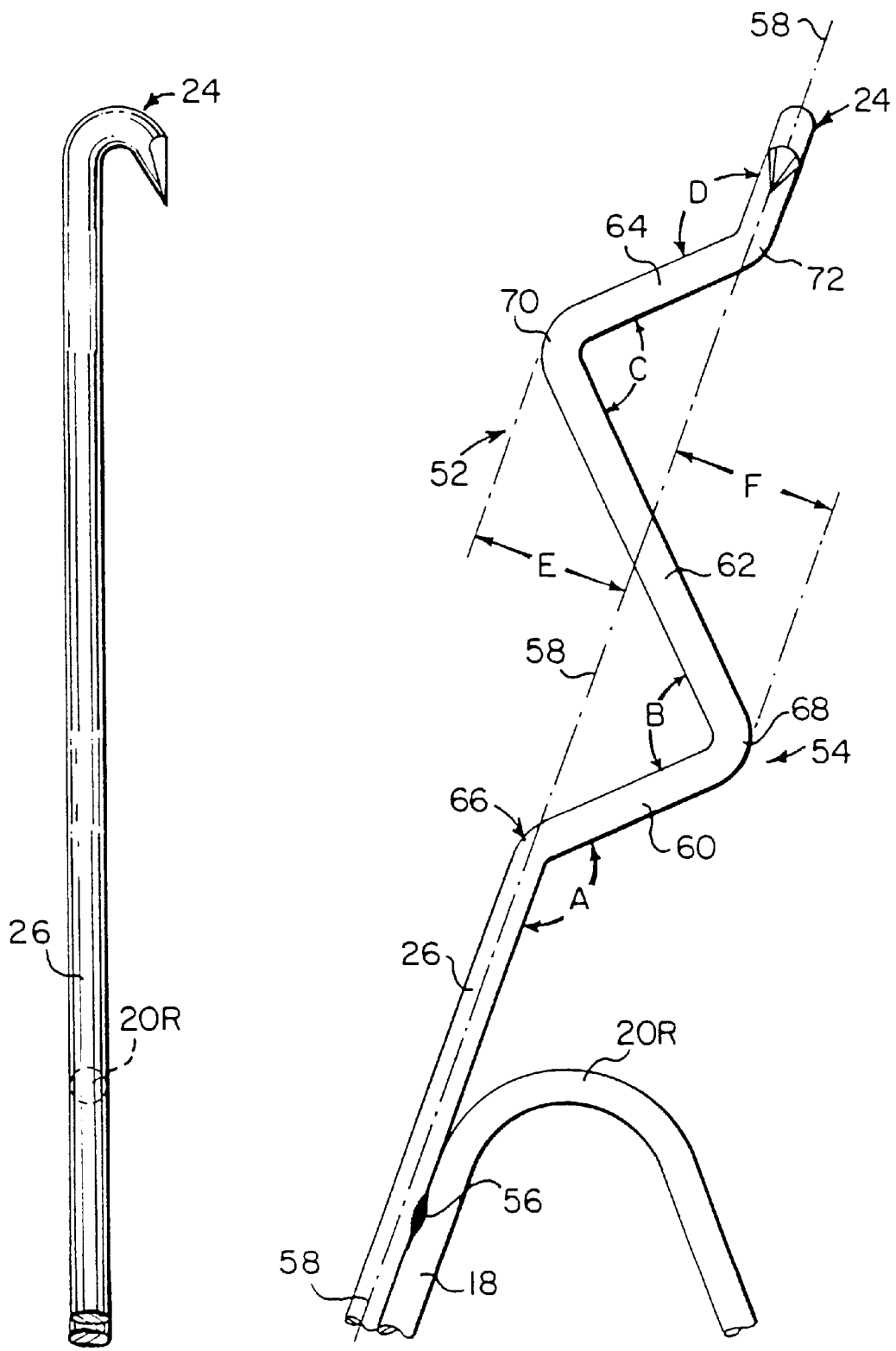
FIG. 11 is an illustration of one embodiment of a hook and hook support attached to a portion of the anchor as seen from a location radially outward of the anchor and viewed in a radially inward direction.
FIG. 12 is an illustration of the hook support of FIG. 11 as seen from the left of FIG. 11 and as viewed in a generally tangential direction.
Figure 13:
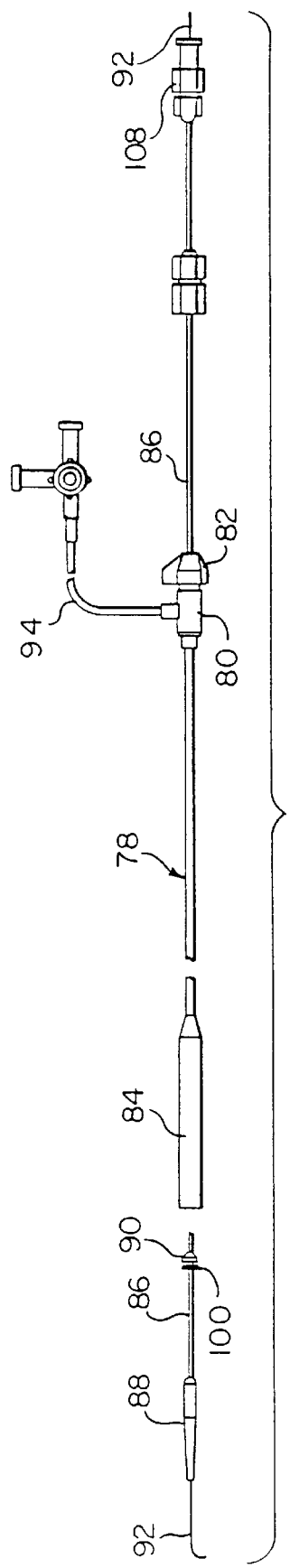
FIG. 13 is an illustration of the delivery apparatus for delivering and deploying the endoprosthesis.

In one specific embodiment illustrated in FIGS. 6, 7, 11 and 12, the transverse extensions, indicated generally at 52, 54 may be formed directly in the hook supports 26 by shaping them to include an S-shaped configuration as shown best in FIG. 11. The lower end of the hook support 26 is welded to one of the wire segments 18, as indicated at 56 (FIG. 12). The wire segment 26 may be considered as having a centerline 58. A portion of the hook support 26, between the hook 24 and the anchor bend 20R is bent into the S-shaped configuration to include first, second and third legs 60, 62, 64, respectively arranged to define the S-shaped pattern. The legs 60, 62, 64 may lie essentially in a single plane that includes the centerline 58, the plane extending approximately tangentially to the outer periphery of its associated anchor 14. The legs 60, 62, 64 are defined by a series of bends 66, 68, 70 and 72. The portion of the hook support 26 that extends distally of the bend 72 is disposed along the center line 58 in alignment with that portion of the support 26 that is proximal of the bend 66. By way of example, the angles A, B, C and D that define the bends 66, 68, 70, 72 may be 135°, 90°, 90° and 135°, respectively. It should be understood, however, that the angles defined by the bends, the lengths of the legs and extent of transverse extensions 52, 54 may be varied for different sizes and uses for such endoprostheses.

The extent to which the transverse extensions 52, 54 extend from the center line 58 may be varied. The degree of extension is illustrated in FIG. 11 by the reference characters E, F. As described more fully below, it is important that the transverse extensions 52, 54 define a distance E+F that will assure the retraction of the hook 24 to its intended low profile, radially inwardly disposed configuration.

FIGS. 13–18 illustrate a catheter-like device by which the endoprosthesis may be percutaneously inserted and deployed within the patient's blood vessel. The delivery device includes an elongate, flexible tubular sheath 78. The sheath may be formed from a suitable polymeric material and has a fitting 80, including a wing nut 82, at its proximal end. The sheath 78 preferably is formed with a small diameter to enhance its flexibility and to include, at its distal end, a tubular pod 84 adapted to receive the endoprosthesis in a low profile radially contracted configuration. The distal end of the sheath thus defines a tubular receptacle into which the endoprosthesis can be loaded and from which it can be deployed. The sheath 78 receives a positioning tube 86 that has, at its distal end, a flexible distally tapered dilator 88 and a stay 90 (FIG. 14) located proximally of the dilator 88. The proximal end of the dilator 88 may be dimensioned to be received within the distal end of the pod 84 as suggested in FIG. 14.

The positioning tube 86 is longer than the sheath 78 so that when assembled, the proximal end of the tube 86 will protrude proximally of the wing nut 82. The positioning tube 86 is adapted to receive a guidewire 92 that may be used to facilitate placement of the device as well as to provide the longitudinal stiffness (column strength) necessary to push the device along its intended path. The positioning tube 86 preferably is formed from a material having "pseudoelastic" or "superelastic" characteristics, such as a nickel-titanium alloy (nitinol). The form of nitinol employed should display superelastic characteristics such that when the device encounters a very sharp or tortuous bend, the positioning tube 86 can flex readily to accommodate the bend without causing a permanent set in the alloy. Superelasticity is a characteristic of some metals that display an unusual ability to be deformed while still retaining the ability to spring back to its original undeformed shape. Such superelastic metals can be deformed as much as eight or more times as far as a conventional metal while still retaining the ability to completely spring back to the undeformed shape. Such alloys typically show a plateau in their stress-strain curves during unloading. For use in the present invention, a superelastic alloy should be used that will maintain its superelasticity over the full range of body temperatures with which the device can be expected to be used. Tubes of such superelastic nitinol alloy are obtainable from the Raychem Corporation under the designation "alloy BB". The fitting 80 also may be provided with a side arm 94 through which a fluid, such as radiopaque contrast liquid, may be injected into the patient to aid in fluoroscopic visualization during the implantation procedure.

Figure 14:
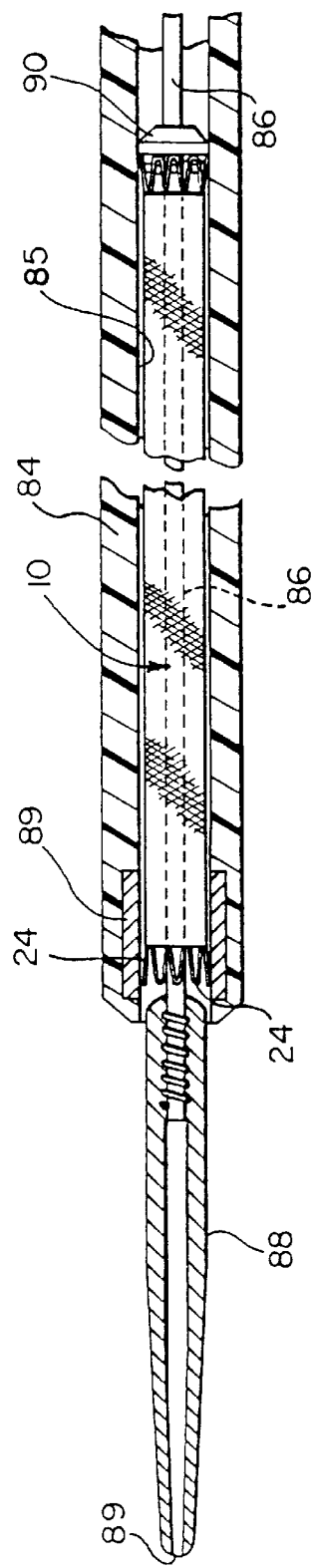
FIG. 14 is an enlarged illustration of the distal region of the delivery device with an endoprosthesis in accordance with the invention loaded and in readiness to be inserted into the patient.
Figure 15:
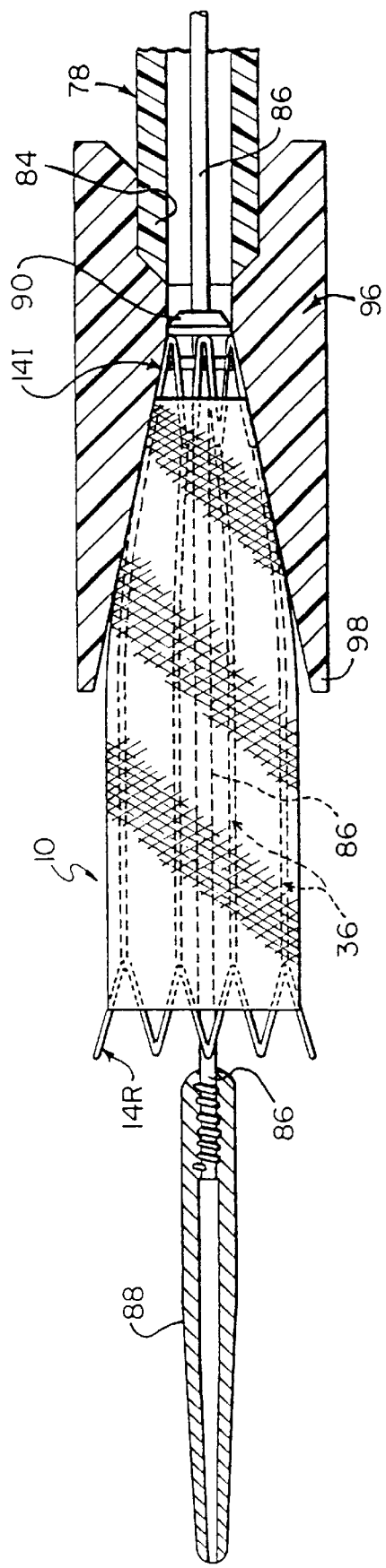
FIG. 15 is a diagrammatic illustration of the manner in which the endoprosthesis may be loaded into the distal end of the delivery device.

When the delivery device and endoprosthesis 10 are arranged in readiness for insertion into the patient, the endoprosthesis will be contained within the pod 84 and about a portion of the positioning tube 86, as illustrated in enlarged detail in FIG. 14. As suggested diagrammatically in FIG. 15, the endoprosthesis may be loaded into the delivery device using a funnel-like loader 96 having an enlarged distal inlet end 98 and a narrowed proximal outlet end 100. When loading the device with the endoprosthesis, the positioning tube 86 is extended through the sheath 78 with its distal end extending beyond the distal end of the pod so that the stay 90 is spaced a short distance from the distal end of the pod 84. The funnel 96 is disposed about the positioning tube 86 with the proximal end of the funnel being in communication with the opening at the distal end of the pod 84. The endoprosthesis is placed over the distal end of the positioning tube 86 so that the proximal bends 20I of the anchor 14I are disposed against the stay 90.

The endoprosthesis and positioning tube 86 then are pulled through the funnel 96 to progressively compress the proximal end of the anchor 14I and move the anchor and stay 90 into the pod 84, thus progressively constricting the endoprosthesis to a low profile about the positioning tube.

The distal tip of the sheath preferably is provided with an inner lining segment 89 formed from the relatively hard material. The lining segment is dimensioned and located to be aligned with the hooks 24 on the distal end of the distal anchor and serves to prevent the hooks 24 from digging into the softer material from which the pod is formed. Additionally, the distal liner preferably is formed from the material sufficiently dense to be observed under fluoroscopy.

Figure 16:
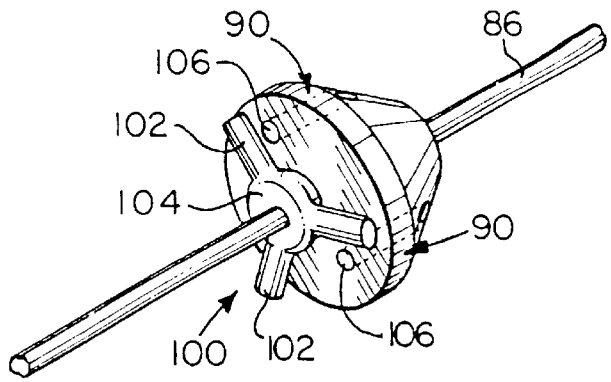
FIGS. 16–18 are illustrations of a section of the delivery device that engages the proximal end of the endoprosthesis.
Figure 17:
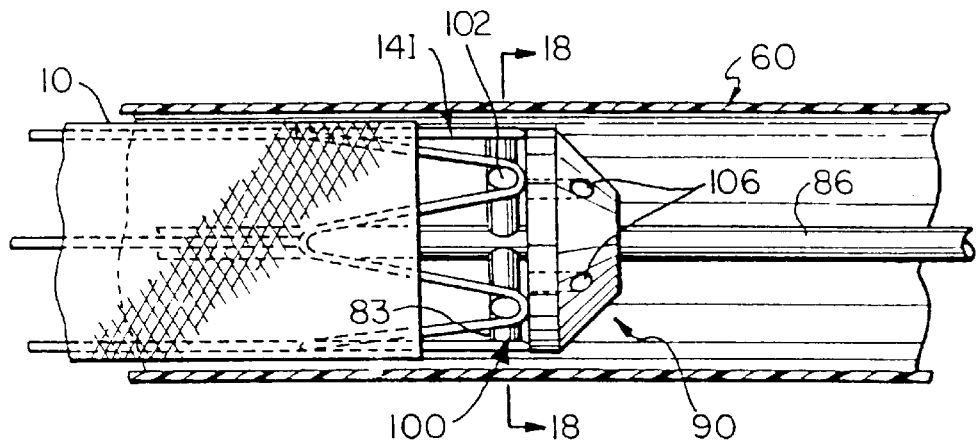
Figure 18:
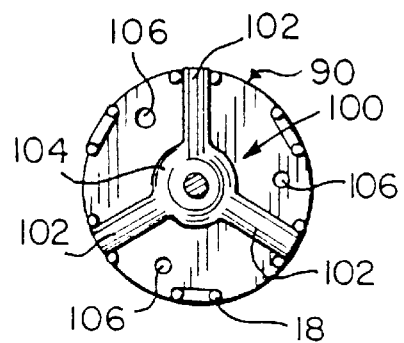

As shown in FIGS. 16–18, the stay 90, that is used to maintain the position of the endoprosthesis 10 as the pod 84 is withdrawn, operation conjunction with a spider-like retainer 100. The retainer 100 may include a plurality of spokes 102 that radiate from a central hub 104. An arrangement of three spokes 102 may be used. The retainer 100 is attached to the positioning tube 86 distally of but close to the stay 90. The diameters of the stay 90 as well as the spokes 102 of the retainer 100 correspond substantially to the diameter of the inner lumen 85 of the pod 84 but are sufficiently smaller to enable the stay 90 and retainer 100 to move freely through the lumen. The spokes 102 of the retainer 100 are arranged to engage the bight defined at the proximal bends 20I of the proximal anchor 14I as illustrated in FIGS. 17 and 18. Thus, the bends 20I may be captured by the spokes 102 of the retainer 100 and the distal face of the stay 90 when the device is loaded in the pod 84. When so loaded, the engagement of the proximal anchor by the stay 90 and retainer 100 assures that the endoprosthesis will remain attached to the delivery device until the pod 84 is completely withdrawn from about the proximal bends 20I of the proximal anchor. Consequently, should it be desired to remove or reposition the endoprosthesis before complete release, the pod 84 may be advanced distally to recapture the endoprosthesis. The stay 90 and retainer 100 may be formed as a single, unitary part.

The delivery device includes two flow channels by which the radiopaque contrast liquid can be injected into the region of implantation. One flow path is defined by the lumen that extends through the positioning tube 86 and dilator 88, opening at an outlet orifice 89 at the distal tip of the dilator 88. A luer fitting 108 on the proximal end of the tube 86 enables connection to an injection device. The second flow path for the radiopaque contrast liquid is through the annular channel defined between the sheath 78 and the positioning tube 86. In order to facilitate flow of radiopaque contrast liquid through that annular channel and past the stay 90, the stay may be formed to minimize resistance to flow through the annular channel, as by providing a plurality of flow apertures, through the stay 90, suggested somewhat diagrammatically at 106. When the endoprosthesis is partially deployed the contrast liquid can be injected through one or both flow paths to enable the physician to observe whether the endoprosthesis has expanded properly and in the desired location within the blood vessel. For example, in treatment of an abdominal aortic aneurysm, if the contrast liquid is observed to travel proximally of the renal (distal) end of the implant, toward the iliac (proximal) end of the device, then the physician can determine that the endoprosthesis has not deployed properly and has not seated properly on the vessel wall. This would indicate a need to retract, reposition or possibly remove the endoprosthesis.

As will be described in further detail, the endoprosthesis is deployed by containing it, in a contracted low profile configuration within a tubular pod 84 at the end of the catheter-like delivery device. The delivery device includes an arrangement that securely engages the proximal (or iliac) end of the endoprosthesis while the tubular pod is withdrawn to progressively expose the end of the prosthesis. As the endoprosthesis is exposed, first at its distal (renal) end, the distal anchor progressively deploys to its expanded configuration with the hooks 24 engaging the tissue wall of the blood vessel. Progressive retraction of the pod causes the more proximal portion of the endoprosthesis similarly to expand radially to its deployed configuration. The deployment device is arranged to retain the proximal end of the proximal anchor while the more distal portions of the endoprosthesis have been deployed. In the event that it is desired to recapture the endoprosthesis, including the hooks at the distal end, within the pod for repositioning or removal from the patient, it is important that the hooks be disengaged from the tissue of the blood vessel smoothly and with minimal injury to the blood vessel wall. Additionally, it is important that the hooks and delivery device be arranged so that when the endoprosthesis is recaptured in the pod, the hooks do not interfere with each other and with the distal opening of the pod as they are retracted radially inwardly and longitudinally within the pod.

Figure 22:
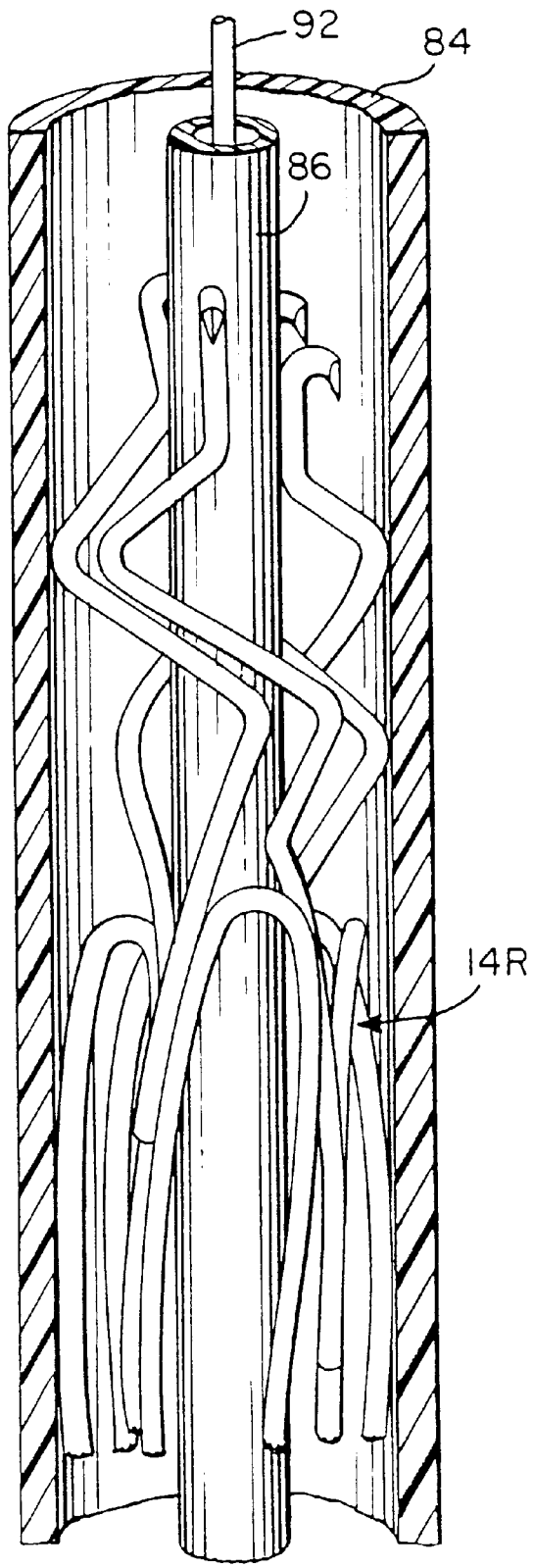
FIG. 22 is an illustration of an anchor having S-shaped hooks as withdrawn into the pod at the distal end of the delivery device.

FIG. 22 illustrates the distal anchor 14R and its hooks 24 retracted within the pod 84. The anchor and the hooks are thus contained within an annular space defined by the pod 84 and an internal positioning tube 86 that forms part of the delivery device. The device is delivered, in this configuration into the patient. By way of example, the outer diameter of the positioning tube 86 may be of the order of 0.050 inches and the inner diameter of the pod 84 may be about 0.188 inches.

Figure 23A:
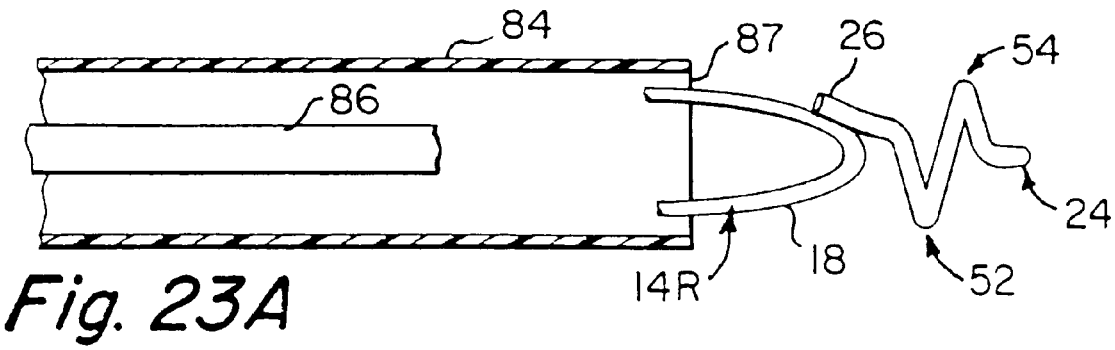
FIGS. 23A–23D illustrate the embodiment incorporating the S-shaped hook supports in various stages of retraction into the sheath.
Figure 23B:
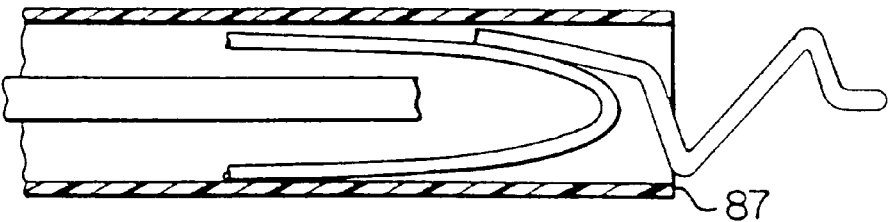
Figure 23C:
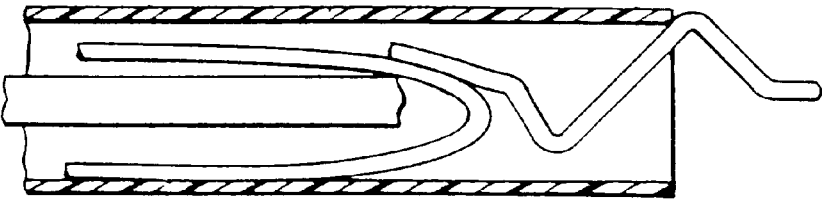
Figure 23D:
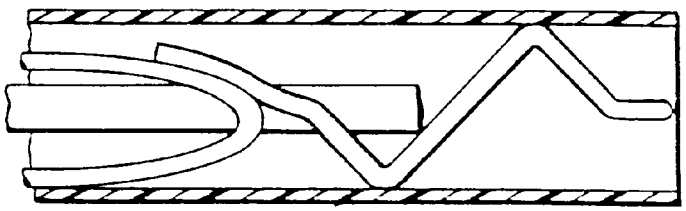
Figure 24A:
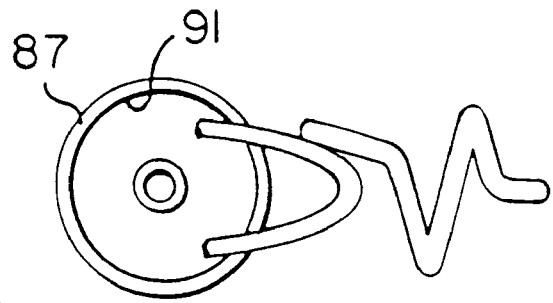
FIGS. 24A–24D are end views of FIGS. 23A–23D, respectively.
Figure 24B:
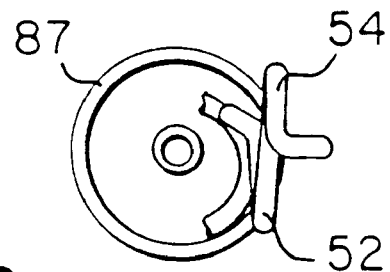

The manner in which the hooks 24 in the embodiments of FIGS. 1, 6, 7, 11 and 12 (having transversely extending elements on the hook supports 26 are retracted into the pod is illustrated in FIGS. 23A–23D and 24A–24D. For ease of illustration only one such hook is shown. FIGS. 23A and 24A show, diagrammatically, the orientation and attitude of a portion of the distal anchor 14R that includes a pair of adjacent wire segments 18 and an attached wire hook support 26. The figures illustrate the distal anchor in a partially deployed position and its progressive retraction to the fully retracted configuration (FIG. 23D) in response to relative movement of the sheath with respect to the prosthesis 10. FIGS. 24A–24D are end views as seen from the right of FIGS. 23A–23D. As shown in FIGS. 23A and 24A, when the hook 24 is disposed in its expanded position, the hook 24 is disposed radially substantially outside of the circumference of the pod 84. As the pod 84 is advanced distally over the anchor, with the positioning tube maintained in a fixed position, (FIGS. 23B, 24B) the rim 87 at the distal end of the pod progressively urges the hook support 26 radially inwardly to cause the hook ends to be drawn radially inwardly toward the central axis of the device.

Figure 24C:
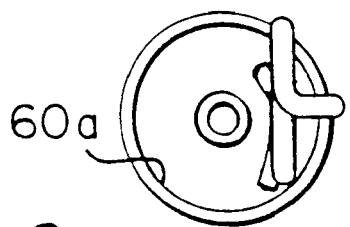
Figure 24D:
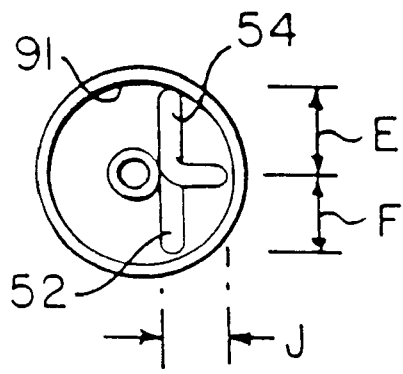

FIGS. 23C and 24C illustrate the configuration after further advancement of the pod in which the distal rim 87 of the pod has engaged one of the transverse extensions on the hook supports defined by a portion of the S-bend in the support 26. As shown in FIG. 24C, this causes the hook 24 to be displaced further radially and transversely with respect to the central axis of the device. As the pod 84 is further advanced relative to the anchor, the distal rim 87 of the pod engages the other transverse extension defined by the other bend in the S-shape so that the extremities of both transverse extensions are drawn radially inwardly and into the annular lumen defined within the pod. FIG. 24D illustrates the transverse extensions disposed within the pod and defining a chordal segment having the length E+F. The combined length E+F is such that the radial projection J of the hook will be well within the circumference defined by the inner surface 91 of the pod. When the hook is so disposed, it then can be drawn easily into the pod without interference with the rim or inner surface 91 of the pod. Thus, the present invention enables an anchor to be contracted from a deployed configuration in which the anchor is fully expanded with its hooks in engagement with the blood vessel wall to a retracted low profile configuration in which the hooks are disposed radially inwardly of the circumference of the pod lumen. By way of representative example, with a pod having an inner diameter of 0.188 inches, a hook support 26 having a diameter of 0.014 inches and with a hook 24 that protrudes 0.030 inches out of the plane of the transverse S-shaped portion, a combined transverse extension E+F of the order of 0.150 inches will be sufficient to draw the tip of the hook substantially radially inwardly of the inner circumference of the pod. In the embodiment shown, E and F each may be of the order of 0.075 inches. It should be understood that other configurations of the transverse extensions may be used to provide the foregoing mode of hook retraction.

Figure 25:
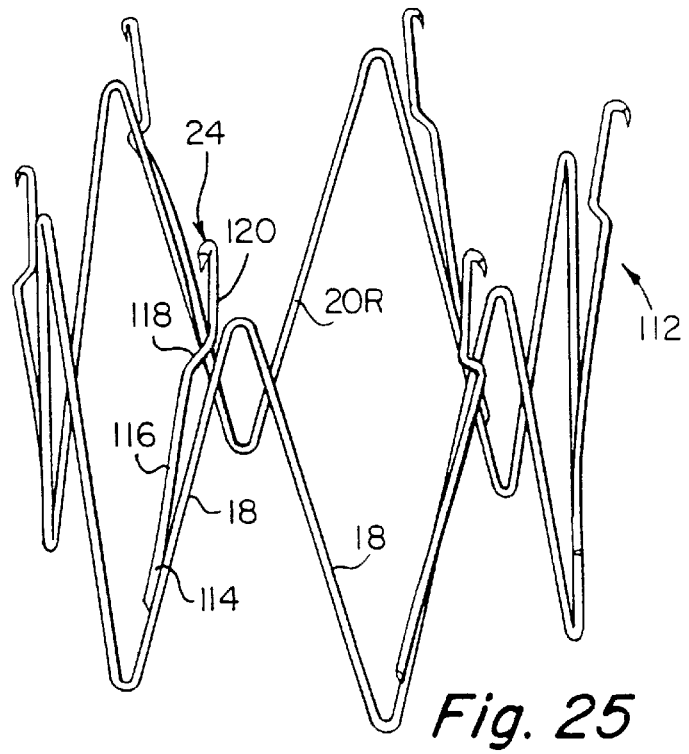
FIG. 25 is an illustration of an anchor with another embodiment of hook supports.
Figures 26, 27:
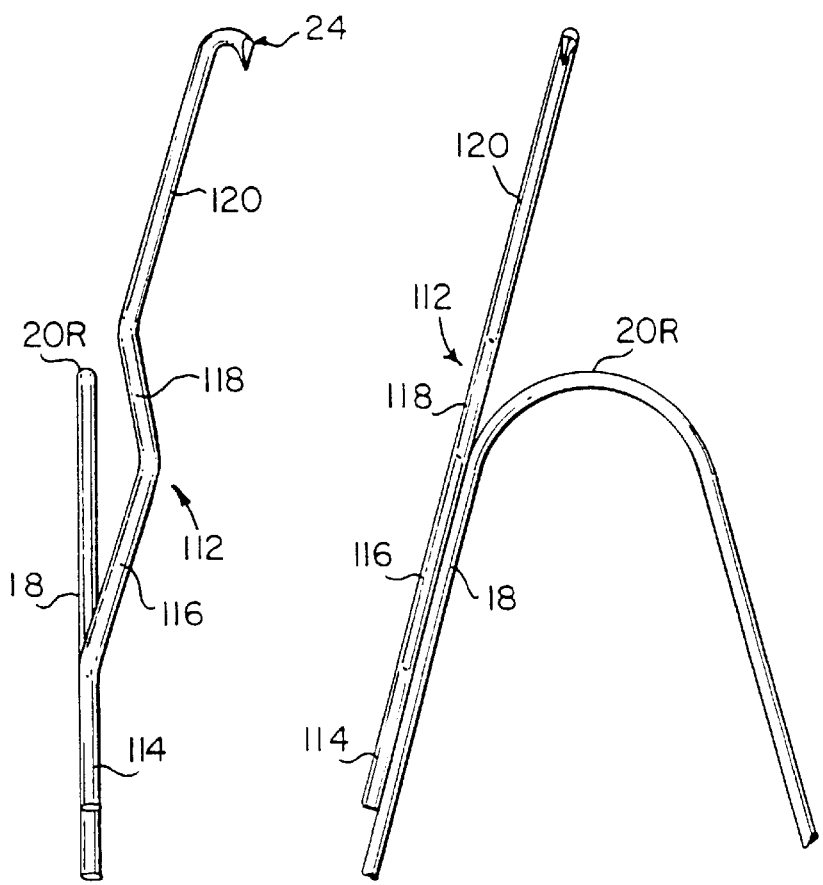
FIG. 26 is an enlarged radially inwardly view of a portion of an anchor and hook support illustrating in further detail the configuration of the hook supports of FIG. 25.
FIG. 27 is a tangential illustration of the embodiment of FIG. 26, as seen from the left of FIG. 26.

FIGS. 25–27 illustrate another embodiment of an anchor having a different hook configuration also adapted to enable the hooks to be withdrawn radially inwardly into the delivery pod 84. In this embodiment, wire hook segments 112 embody a different construction for effecting radially inward camming of the hooks 24 when the device is drawn into the pod. In this embodiment, the hook supports 112 include several sequential portions including an attaching portion 114, a camming portion 116, an offset portion 118 and an extension portion 120, the hook 24 being formed at the distal end of the extension portion 120. As illustrated in further detail in FIGS. 26 and 27, the attaching portion 114 of the hook support 112 is secured, as by welding, to and along a wire segment 18 so that the hook 24 is disposed distally of the bend 20R associated with that wire segment. The hook support 112 may be arranged so that all of its portions 114, 116, 118 and 120 lie in a common plane (FIG. 26). The hook support 112 is attached, at portion 114, so that the hook 24 extends radially outwardly.

FIG. 27 illustrates the configuration of this embodiment when the anchor is in its expanded, relaxed configuration. In that configuration, the camming portion 116 of the wire hook segment 112 can be seen to be disposed preferably at an angle of the order of 15° to the attaching portion 114 so that the camming portion 116 will project radially outwardly of the wire segment 18 by an angle of about 15°. The offset portion 118 defines an angle with respect to the camming portion 116 of the order to 25° preferably with the offset portion 118 being oriented somewhat back toward the main, zigzag portion of the anchor. The extension portion 120, having the hook 24 at its distal end, extends from the end of the offset portion 118 along a line generally parallel to the camming portion 116. Thus, the extension 120 is offset radially inwardly from the camming portion 116. In the illustrative embodiment, an offset of about 5 millimeters has been found satisfactory. It will be appreciated when the pod is advanced in a distal direction over the endoprosthesis, the rim of the pod will engage the camming portion 116 and cause it to flex and bend radially inwardly about the juncture of the attaching portion 114 and camming portion 116. Because the extension portion 120 is offset radially inwardly from the camming portion 116, when the camming portion 116 has been urged into general alignment with its associated wire segment 18 by advancement of the pod over the device, the extension portion 120 and hook 24 will be disposed radially inwardly of the circumference defined internally of the pod. In this regard, it should be noted that the hook 24 is disposed radially inwardly of an extension of the axis of the camming portion 116.

FIGS. 28A–28C and 29A–29C illustrate diagrammatically the progressive movement of a representative hook support 112 as the pod 84 is advanced over the endoprosthesis. FIG. 28A illustrates the attitude of the hook support 112 as the distally advancing pod begins to engage the camming segment 116. FIG. 28B illustrates the arrangement when the pod has advanced along the camming segment 116 sufficiently to orient the camming segment generally along the longitudinal axis of the delivery device, with the hook 24 being disposed radially inwardly of the circumference defined by the inner lumen of the pod. FIGS. 28C and 29C illustrate the configuration of this embodiment when the pod has been advanced fully over the endoprosthesis containing the hook 24 within the pod. It may be appreciated that as the anchor 14R is captured and retracted into the pod 84 the wire segments 18 of the anchor progressively shift from their skew attitude to an attitude that extends generally axially of the device. The hook supports 26, which are secured to the anchor segments 18 similarly shift from their skew attitude to a generally axially aligned attitude that facilitates their being drawn smoothly into the pod 84.

Figure 30:
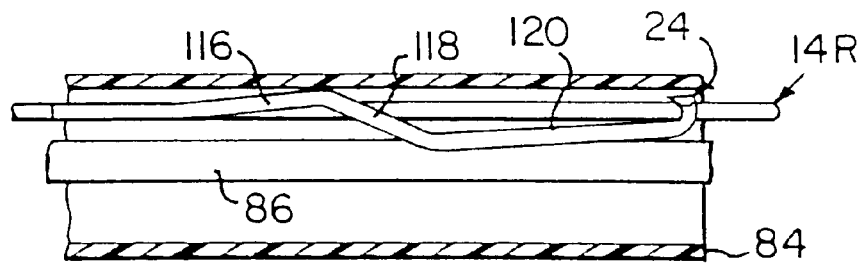
FIG. 30 illustrates, diagrammatically, a modified embodiment of the embodiment as shown in FIGS. 25–29 in a configuration in which it is withdrawn into the delivery device.

FIG. 30 illustrates a further modified embodiment of the invention having essentially identical components and mode of operation as that described above in connection with FIGS. 25 and 29 except that the hook support and extension 120 are arranged relative to the zigzag portion of the anchor so that the hook 24 is disposed proximally of the distal bend 20R. By constructing the device so that the hooks are disposed proximally of the distal end of the anchor, the anchor segments themselves may reduce the risk of hook entanglement. As with all embodiments, hooks may be formed on any number of wire segments as may be considered desirable for a particular medical procedure.

Figure 31:
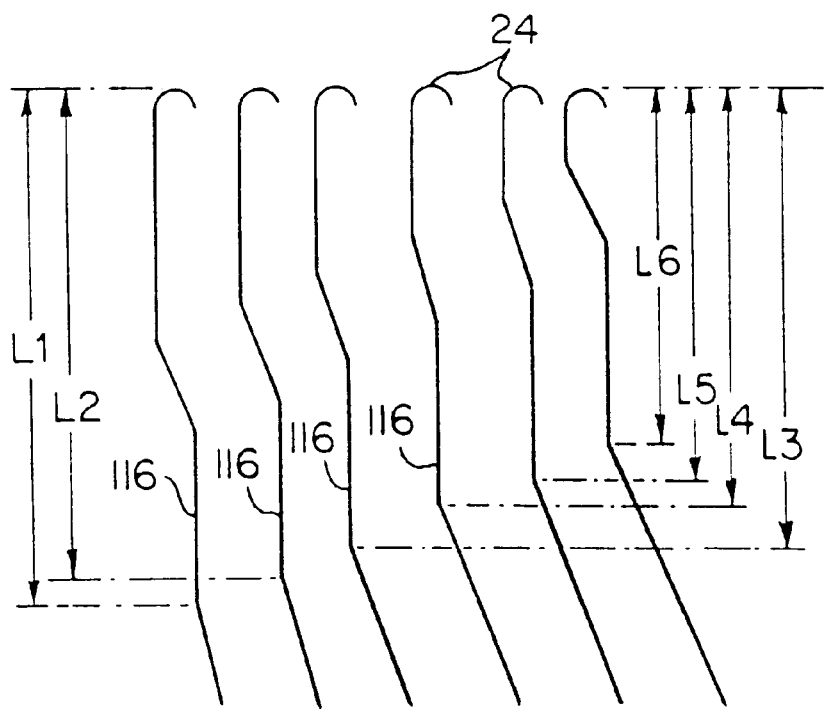
FIGS. 31 and 32 are diagrammatic illustrations of an array of hook supports of the type illustrated generally in FIGS. 26–30 in which the hook supports are provided with a means to vary the sequence in which the hook supports are drawn radially inwardly to a contracted configuration.
Figure 32:
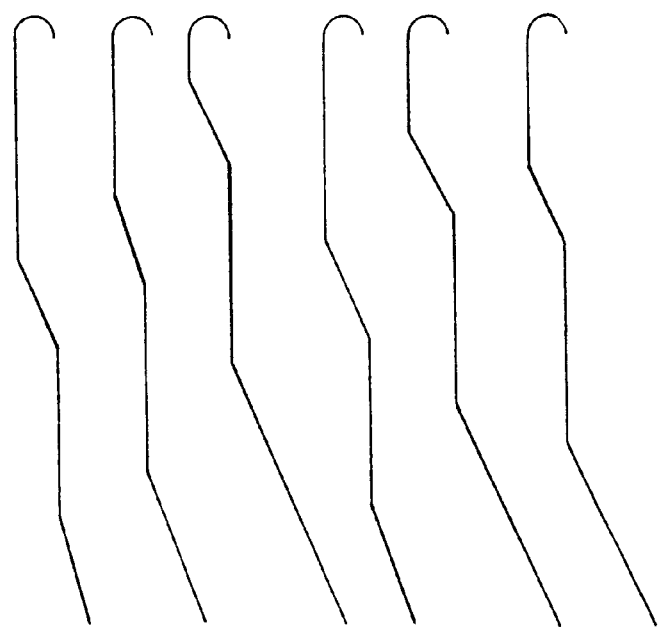
Figure 35:
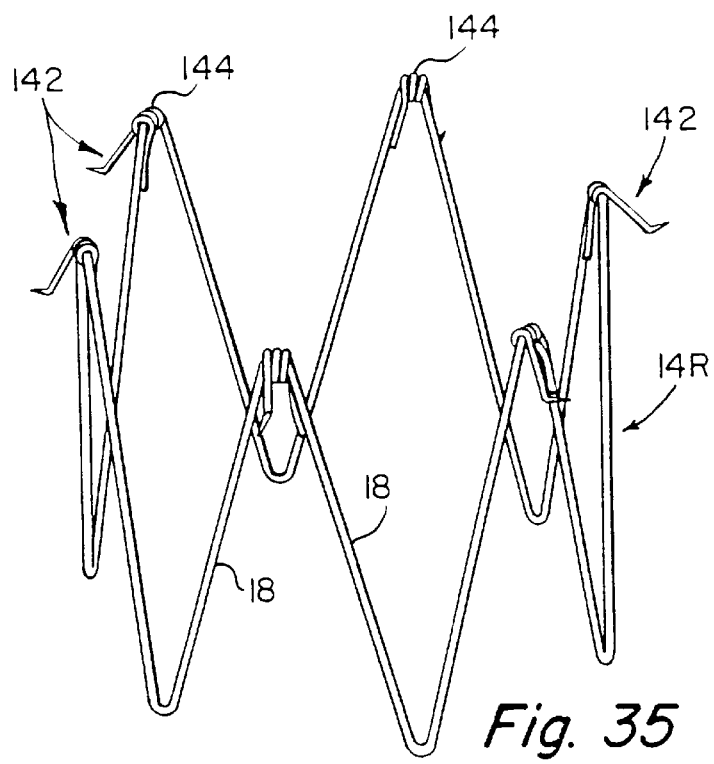
FIG. 35 is an illustration of an anchor having another embodiment of hook assembly.
Figure 36:
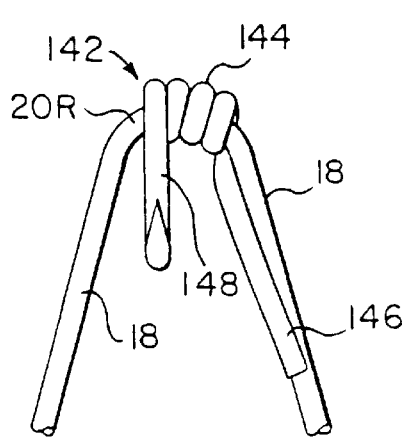
FIG. 36 is an enlarged illustration of the hook assembly of FIG. 35.

The invention may be further modified so that the hooks 24 are drawn radially inwardly in a predetermined sequence rather than simultaneously. By sequencing the radially inward retraction of the hooks 24, the risk of hooks becoming entangled with each other may be further reduced. The relative sequence in which the hooks are urged radially inwardly may be determined as illustrated diagrammatically in FIGS. 31 and 32 which illustrate, diagrammatically, the pattern of hook support 112 adapted to effect the sequential operation. FIG. 31 illustrates a series of six hook supports in the order (as seen from left to right) that they would be disposed circumferentially about the anchor. The camming portion 116 in each of the segments 112 is disposed a different distance (L1–L6) from the hooks 24. FIG. 31 shows an arrangement in which the distance decreases from one segment to the next in a circumferential direction. It will be appreciated that with hook segments so configured, the camming portions 116 will be engaged by the pod at different times in a circumferentially progressive sequence as the pod is progressively advanced over the endoprosthesis. That results in circumferentially sequential retraction of the hooks. FIG. 32 similarly discloses such an arrangement but in which the distances between the camming sections and the hooks are in a somewhat staggered pattern.

Figures 33, 34:
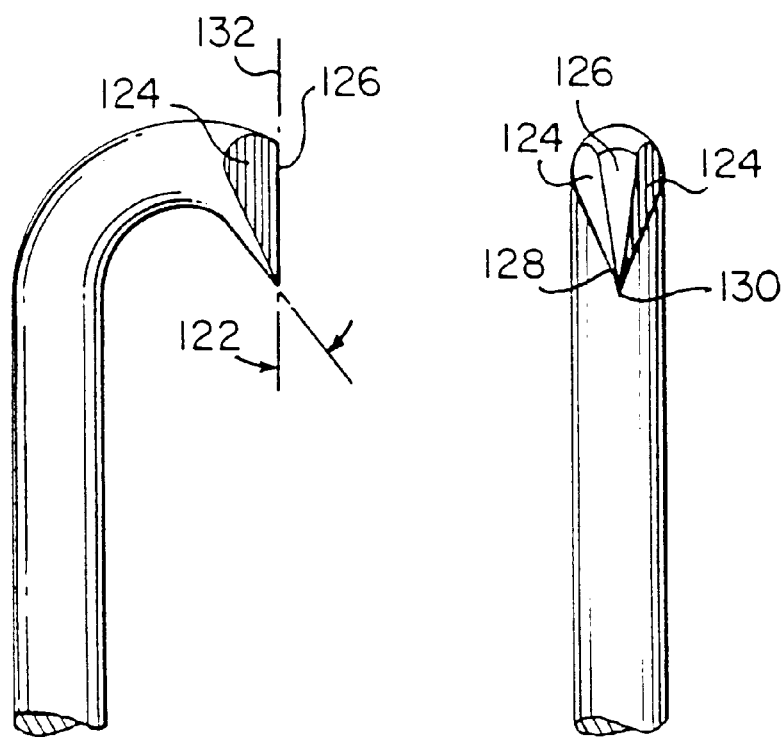
FIG. 33 is a side elevation of one type of hook that may be used in the invention.
FIG. 34 is a side elevation of the hook as seen from the right of FIG. 33.

FIGS. 33 and 34 illustrate a preferred embodiment for the structure of the hook 24. It is desirable that the hook have a very sharp point readily adapted to pierce tissue with minimal trauma. Similarly, the hook should be configured to be removed from engagement with the tissue, also with minimal trauma. Additionally, it is important that the hook be configured so that it will not pierce the wall of the pod if, for example, the pod is squeezed or otherwise subjected to an unexpected stress tending to compress the pod wall against the hook. As shown in FIGS. 33 and 34, the distal end of the wire hook segment 26 or 112 is bent to a curved configuration. The arch defined by the curved hook may define an angle 122 of between about 25° and 45° with an angle of about 30° being preferred. The tip of the hook is formed to a very sharp point by grinding three facets on the end of the hook, including a pair of side facets 124 and a middle facet 126. The side facets 124 meet at a jointed defined by an edge 128 that terminates at and defines a sharp point 130. In this embodiment, the angle 122 and facets 124, 126 are formed so that the middle facet 126 and edge 128 extend along a plane, indicated in phantom at 132, that will extend substantially parallel to the longitudinal axis of the endoprosthesis and the pod 84 when the device is contained within the pod. With this configuration, if the pod is pressed against a hook 24, it will engage the relatively planar surface 126 with substantially reduced risk of the points 130 striking through the wall of the pod. By way of further example, in the illustrative embodiment in which the hook support and hook are formed from a wire having a diameter of the order of 0.014", the length of the middle facet 126 preferably is of the order of about 0.025 inches. The included angle of the side facets 124, 126 may be about 120°. The throat of the hook, which defines the radial penetration depth of the hook is measured from the sharp point to the hook support, may be of the order of 0.030 inches.

FIGS. 35–38 illustrate another embodiment of the invention by which hooks carried by the anchor are movable between the radially outwardly projecting deployed configuration and a contracted configuration contained with the pod. In this embodiment, one or more hook assemblies indicated generally at 142 are attached to one or more distal bends 20R of the distal anchor 14R. The hook assemblies 142 include a torsion spring 144 arranged to urge the hook assembly 142 to a deployed configuration illustrated in FIGS. 37–39. The hook assemblies 142 may be formed from a length of wire to include the helically coiled torsion spring 144, a tail 146 extending from one end of the spring 144 and a shank 148 formed at the other end. The end of the shank 148 is bent as indicated in FIG. 39 to define a hook tip 150 with a sharp point 152. The tail 146 may be attached securely to one of the wire segments 18 of the anchor with the spring coil 144 wrapped about the distal bend 20R. The hook assembly 142 is constructed so that when relaxed, the spring 144 will bias the shank 148 and tip 150 in a configuration shown in which the tip 150 is angled slightly downwardly.

The wire that forms the hook assembly 142 may, for example, be formed from MP35N alloy having a diameter of 0.012 inches. As adequate biasing force may be developed with a torsion spring 142 having twelve helical turns.

Figure 37:
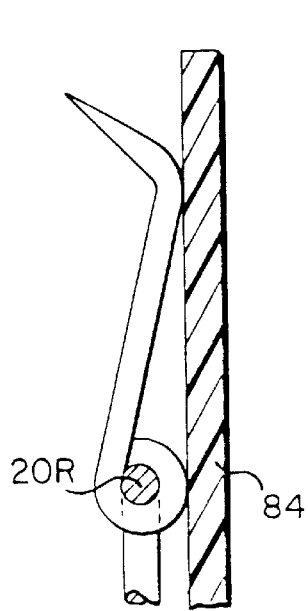
FIG. 37 is a diagrammatic illustration of the configuration of one of the hooks assemblies in FIG. 35 when the device is contained within a sheath.
Figure 38:
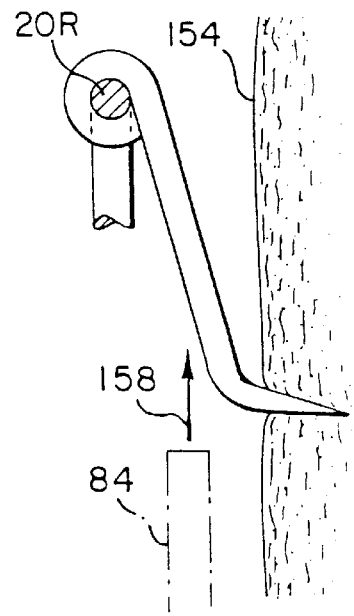
FIG. 38 is a diagrammatic illustration similar to FIG. 37 showing the manner in which the hook assembly of FIG. 37 engages the tissue of a body lumen when the device is deployed within the patient.

FIGS. 37 and 38 illustrate, diagrammatically, the manner in which the hook assemblies are contained within the pod 84 and the manner in which they engage the tissue 154 of the blood vessel. When contained within the sheath 84, the sheath urges the shank 148, in opposition to the torsional force of the spring 144, so that the shank 148 extends generally in a distal direction. The angle between the shank 148 and tip 150 is selected to define a heel 156 that, when the device is engaged and contained within the pod 84, will bear against the inner surface of the pod 84. Thus, the sharp tip 152 is maintained out of engagement with the pod. The angle defined at the heel should be such to assure that the point 152 will not engage the pod 84 throughout the full range of movement of the pod to release or capture the hook assemblies 142. FIG. 38 illustrates the manner in which the hook assemblies 142 engage the tissue or blood vessel 154 when implanted. The device is dimensioned and constructed so that it will engage the tissue 154 as the spring 144 has urged the shank to its fully relaxed position. The spring 144 assumes that the point 150 will firmly engage the tissue 154 to maintain the secure connection.

Should it be desirable to recapture the endoprosthesis before it is completely deployed, the pod 84 (shown in phantom in FIG. 38) may be advanced distally (arrow 158) over the endoprosthesis. As the advancement of the pod progressively contracts the endoprosthesis, including the distal end of the distal anchor 14R, the distal bends 20R, to which the hook arrangement 42 is attached will be drawn progressively radially inwardly. Continued advancement of the pod will cause the hook tip 150 to withdraw from the tissue 154. The rim of the pod 84 then can engage the shank 148 to urge the device to the retracted configuration as shown in FIG. 37.

Figure 39A:
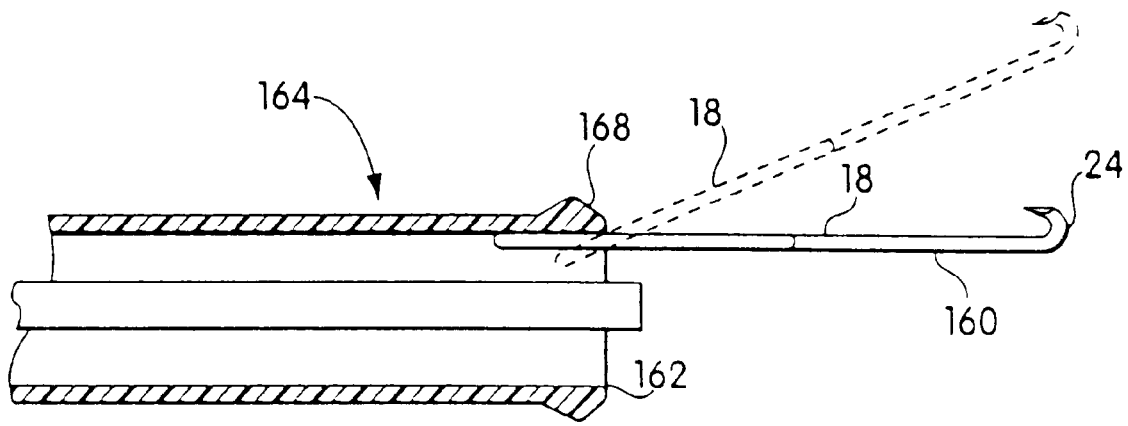
FIGS. 39A–39C are sequential diagrammatic illustrations of another embodiment of the invention in which the hooks are arranged to engage the distal rim of the pod in the delivery device in a manner that prevents exposure of the sharp tips of the hooks.
Figure 39B:
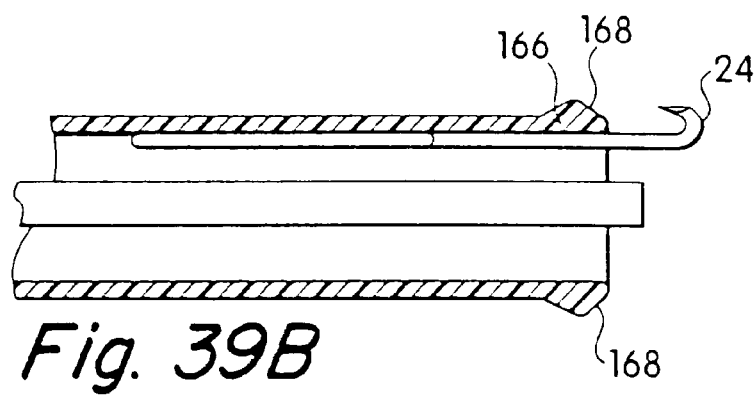
Figure 39C:
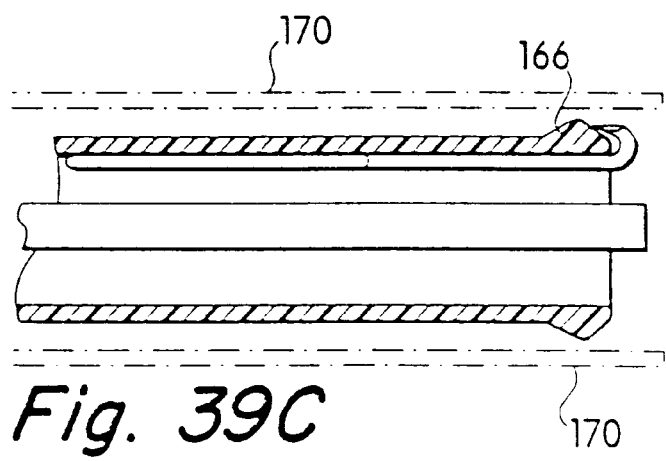

FIGS. 39A–39C illustrate, diagrammatically, another embodiment of a hooked anchor and pod 164 adapted for use with the anchor in which the anchor can be collapsed and contained within the pod. In this embodiment, the hooks themselves are not drawn fully into the pod but, instead, are engageable with a specially contoured distal end so that the sharp tips are not exposed. In this embodiment the anchor is provided with wire hook supports 160 that are substantially straight and formed to define hooks 24 at their distal ends. The hook supports 160 are secured to associated wire segments 18 of the anchor, as by welding. As with the previously described embodiments, FIGS. 39A–39C are simplified illustrations of the change in attitude and position that one of the hooks on the anchor makes as the pod is advanced over the endoprosthesis. FIG. 39A illustrates in phantom the attitude of the hooked anchor as it is initially engaged by the rim 162 of the pod 164. The hooked anchor is illustrated, diagrammatically in solid in FIG. 39A to illustrate the approximate attitude of the device after the pod has been advanced somewhat further over the proximal portion of the anchor, from which it can be seen that the anchor, segment 160 and hook 24 have been urged radially inwardly. FIG. 39B illustrates a further state of advancement of the pod 164 over the hooked anchor. It can be seen that once the anchor has been withdrawn sufficiently into the pod 164 so that it is in a reduced diameter, generally cylindrical configuration, the hooks 24 will not advance further radially inwardly. Rather, as the pod 164 is advanced over the endoprosthesis, its rim 162 will advance directly toward and into engagement with the hooks 24, as shown in FIG. 39C. In accordance with this embodiment, the distal end of the pod 164 is provided with a circumferential flange 166 having a distally tapering surface 168 that is contoured to engage the point (which may be identical to the point 130) so that the point is not exposed in a manner that could catch on tissue or other elements.

In a further aspect of the invention, the delivery device may be modified to include an additional sheath adapted to receive the pod as suggested diagrammatically in phantom at 170 in FIG. 39C. This embodiment of the invention may be used, for example, with the type of pod and hook arrangement illustrated in FIGS. 39A–39C in order to provide an additional measure of protection for the hooks 24. It may be used, however, with other embodiments, if desired.

The delivery device properly loaded can be inserted into and through the patient's vasculature with the aid of a guidewire. The guidewire 92 may be preliminarily loaded into the lumen of the positioning tube 86 before the delivery device is inserted into the patient or, alternately, the guidewire may be placed separately, in a preliminary procedure, into the patient's blood vessel. In either case, the delivery device is advanced into the patient's blood vessel, for example, as through the femoral artery, when placing a graft assembly to treat an abdominal aneurysm. The guidewire may be advanced independently toward and through the region to be treated. The delivery device then may be advanced over the guidewire until the endoprosthesis is in its intended position.

In the treatment of an abdominal aortic aneurysm with the invention, the endoprosthesis would be located so that the renal anchor 14R is located on the renal side of the aneurysm (see FIG. 6) such that the endoprosthesis, when deployed, is disposed along the aneurysm thereby lining the aorta. With the delivery device so placed, the position of the positioning tube 86 is maintained while the sheath and pod 84 are withdrawn in a proximal direction. The stationary stay maintains engagement with the iliac end of the anchor 14I in the manner described above, thereby preventing movement of the endoprosthesis in the iliac direction while the pod is withdrawn. As the pod is progressively withdrawn and the renal anchor 14R emerges from the distal end of the pod, the anchor 14R expands into engagement with the inner lumen surface of the blood vessel while simultaneously expanding the distal end of the graft. As the anchor 14R expands, its hooks 24 engage the inner luminal surface of the blood vessel.

The endoprosthesis and delivery device enable the endoprosthesis to be removed or repositioned within the patient before completing the deployment process. As long as the proximal portion of the implant remains connected to the delivery device the deployment process can be reversed to recapture the endoprosthesis within the pod so that it can be repositioned and redeployed or withdrawn from the patient. Throughout the procedures, fluoroscopic or X-ray visualization methods can be used to determine if the implant is positioned as desired.

If the endoprosthesis is positioned as desired, the pod 84 is withdrawn completely thereby releasing the endoprosthesis and allowing it to expand fully into contact with blood vessel along the full length of the endoprosthesis. If, before full release, it is determined that it is not positioned exactly as desired, the pod can be advanced distally to recapture the endoprosthesis. The recapture the endoprosthesis and the pod can be accomplished with any of the embodiments of the invention, including those where there is a single anchor that extends clearly the length of the graft as well as those illustrated in the drawings which there are proximal and distal anchors connected by struts.

Figure 19:
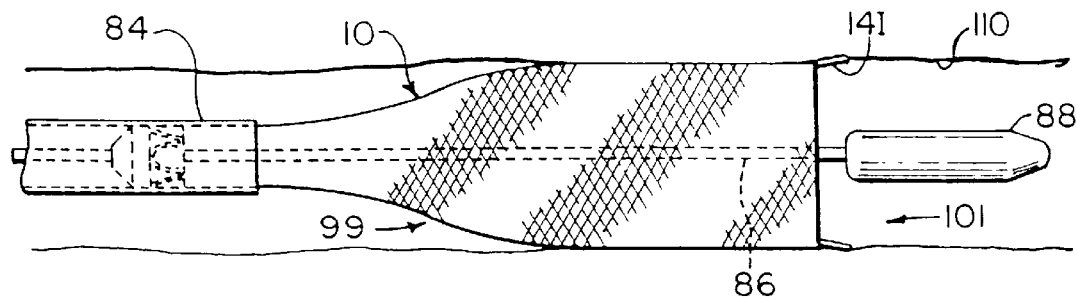
FIGS. 19–21 are diagrammatic illustrations of the process by which the endoprosthesis may be recaptured during a delivery procedure to enable it to be repositioned or removed from the patient.
Figure 20:
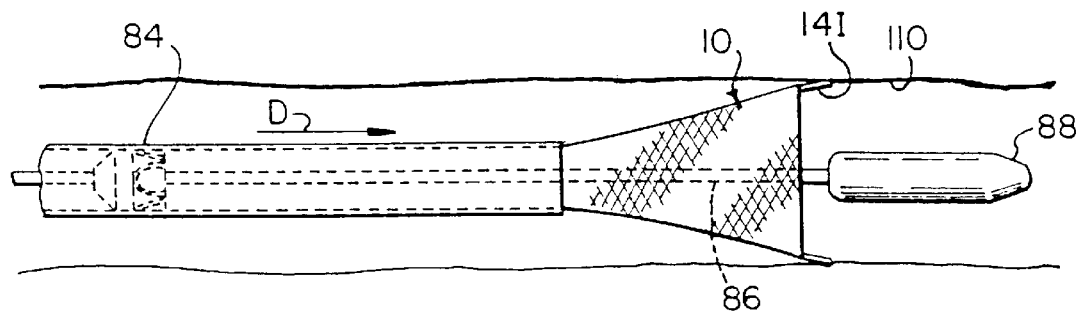
Figure 21:
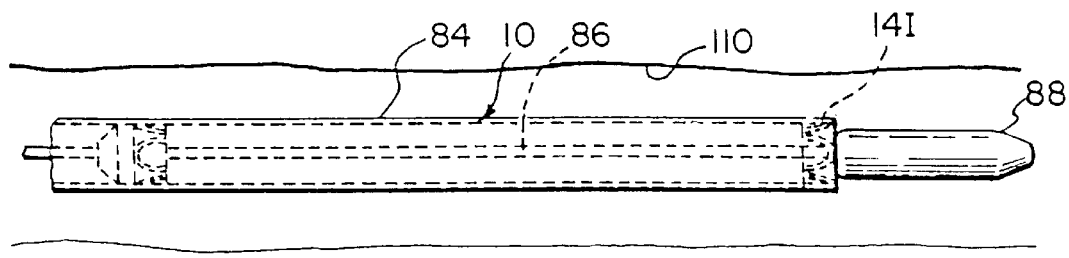

FIGS. 19–21 depict the implant repositioning or removal process described above. In FIG. 19, an endoprosthesis 10 disposed within the pod 84 is shown as being partially released from the pod 84. The renal end of the implant has deployed and is seated against the inner surface of the lumen of the blood vessel. If, at this point, it is determined, such as by fluoroscopic visualization, that repositioning or removal of the implant is required, the sheath and pod 84 can be advanced in the renal direction (to the right in FIGS. 19–21) to progressively recapture the endoprosthesis. As shown in FIG. 20, the pod 84 has been advanced to radially compress and recapture a portion of the endoprosthesis 10. FIG. 21 shows the pod advanced over the entire length of the endoprosthesis. In so doing, the implant has been removed from contact with the vessel wall and can be removed from the patient or positioned at a different location.

Thus, it will be appreciated that the invention provides improved devices and techniques for placing, anchoring and repositioning an endoprosthesis and, particularly, an endoprosthesis having hooks adapted to dig into and engage the tissue that defines the body lumen into which the endoprosthesis is to be deployed.

It should be understood, however, that the foregoing description of the invention is intended merely to be illustrative thereof and that other embodiments, modifications and equivalents may be apparent to those skilled in the art without departing from its spirit. It should be understood, therefore, that the scope of the invention is not confined to the specific embodiments illustrated and described herein but, rather, that the scope be determined by the following claims and their equivalents.

We claim:

1. A vascular endoprosthesis comprising:

a flexible tubular graft having proximal and distal ends;

an anchor assembly attached to the graft, the anchor assembly having a proximal end, a distal end and an axial length at least equal to that of the graft, at least the proximal end and distal end of the anchor assembly being resiliently expandable and connected to each other by at least two longitudinal struts that are oriented askew to the axis of the anchor assembly when the assembly is expanded.

2. An apparatus as defined in claim 1 wherein the ends of the anchor assembly include anchors formed from wire arranged in a zigzag, generally tubular configuration of alternating anchor segments and bends, each of the anchor segments being arranged skewed to the longitudinal axis of the anchors when the anchors are expanded, the ends of each of the longitudinal struts being attached to and defining extensions of one of the anchor segments.

3. An endoprosthesis as defined in claim 1 further comprising:

the struts comprising a core wire and a wire helically wound about the core.

4. An endoprosthesis as defined in claim 3 further comprising:

a polymeric layer extending over the helical wire along the strut.

5. An endoprosthesis as defined in claim 4, wherein the polymeric layer is formed from a material that is bondable to the graft, the anchor assembly being attached to the graft by bonding at least portions of the polymeric layer of the struts to the graft.

6. An endoprosthesis as defined in claim 5 wherein said polymeric material is heat bondable to the graft and is attached to the graft by such heat bonding.

7. An endoprosthesis as defined in claim 2 further comprising:

the struts comprising a core wire and a wire helically wound about the core.

8. An endoprosthesis as defined in claim 7 further comprising:

a polymeric layer extending over the helical wire along the strut.

9. An endoprosthesis as defined in claim 8 wherein the polymeric materials is heat bondable;

the polymeric layer being formed from a material that is heat bondable to the graft, the anchor assembly being attached to the graft by heat bonding at least portions of the polymeric layer of the struts to the graft.

10. A vascular endoprosthesis adapted to be delivered into and deployed in a blood vessel by a delivery device that includes a tubular sheath at its distal end, the endoprosthesis comprising:

a tubular elongate graft having proximal and distal ends;

a resiliently expandable anchor assembly having proximal and distal ends and a longitudinal axis, the anchor assembly being attached to the graft, the anchor assembly being radially expandable and contractible between an expanded position in which it supports the tubular graft in an open configuration and a radially contracted configuration in which the anchor assembly has a substantially reduced cross-sectional profile to enable the endoprosthesis to be radially contracted and contained within the delivery sheath;

at least one hook attached to the anchor assembly and arranged to project radially outwardly, the hooks being mounted to the anchor assembly so that when the anchor assembly is in its expanded position, the hooks will be disposed radially outwardly of the graft and when the anchor is in a contracted configuration, the hooks can be disposed radially inward of and be contained within the delivery sheath;

said at least one hook having a configuration comprising a bight portion that extends from the hook support and terminates in a sharp tip, the tip being defined by three facets formed at the end of the bight, including a middle facet and a pair of side facets, the middle and side facets merging together to define the sharp tip of the hook, the middle facet being oriented such that, when the anchor assembly is contained within the sheath, the middle facet will lie in a plane that is parallel to the longitudinal axis of the sheath.

11. An endoprosthesis as defined in claim 10 wherein the throat of the hook is of the order of 0.030 inches and the length of the middle facet is about 0.025 inches.

12. A vascular endoprosthesis comprising:

a flexible tubular graft having proximal and distal ends;

an anchor assembly attached to the graft, the anchor assembly having a proximal end, a distal end and an axial length at least equal to that of the graft, at least the proximal end and distal end of the anchor assembly being resiliently expandable and connected to each other by at least two longitudinal struts;

the struts further comprising a core wire and a wire helically wound about the core wire.

13. An endoprosthesis as defined in claim 12 further comprising:

a polymeric layer extending over the helical wire along the strut.

14. An endoprosthesis as defined in claim 13 wherein the polymeric layer is formed from a material that is heat bondable to the graft, the anchor assembly being attached to the graft by heat bonding at least portions of the polymeric layer of the struts to the graft.

* * * * *